US007977457B2

(12) United States Patent
Reiter et al.

(10) Patent No.: US 7,977,457 B2
(45) Date of Patent: Jul. 12, 2011

(54) FUSION PROTEINS, USES THEREOF AND PROCESSES FOR PRODUCING SAME

(75) Inventors: Yoram Reiter, Haifa (IL); Roy Noy, Ganei Yehuda (IL); Kfir Oved, Givataim (IL)

(73) Assignees: Teva Pharmaceutical Industries Ltd., Petah Tikva (IL); Technion Research & Development Foundation Ltd., Haifa (IL)

( * ) Notice: Subject to any disclaimer, the term of this patent is extended or adjusted under 35 U.S.C. 154(b) by 608 days.

(21) Appl. No.: 11/804,541

(22) Filed: May 17, 2007

(65) Prior Publication Data

US 2008/0014208 A1      Jan. 17, 2008

Related U.S. Application Data

(60) Provisional application No. 60/801,798, filed on May 19, 2006.

(51) Int. Cl.
    *C07K 14/00*   (2006.01)
    *C07K 17/14*   (2006.01)
    *C07K 17/00*   (2006.01)

(52) U.S. Cl. ..................................... 530/350; 530/391.1

(58) Field of Classification Search .................. None
    See application file for complete search history.

(56) References Cited

U.S. PATENT DOCUMENTS

| | | | |
|---|---|---|---|
| 4,855,237 A | 8/1989 | Morinaga et al. | |
| 5,194,425 A | 3/1993 | Sharma et al. | |
| 5,260,422 A | 11/1993 | Clark et al. | |
| 5,284,935 A | 2/1994 | Clark et al. | |
| 5,468,481 A | 11/1995 | Sharma et al. | |
| 5,635,363 A | 6/1997 | Altman et al. | |
| 5,820,866 A | 10/1998 | Kappler et al. | |
| 5,837,477 A | 11/1998 | Germain et al. | |
| 5,869,270 A | 2/1999 | Rhode et al. | |
| 5,976,551 A | 11/1999 | Mottez et al. | |
| 6,011,146 A | 1/2000 | Mottez et al. | |
| 6,015,884 A | 1/2000 | Schneck et al. | |
| 6,140,113 A | 10/2000 | Schneck et al. | |
| 6,153,408 A | 11/2000 | Abastado et al. | |
| 6,211,342 B1 | 4/2001 | Hirsch et al. | |
| 6,232,445 B1 | 5/2001 | Rhode et al. | |
| 6,248,564 B1 | 6/2001 | Walter et al. | |
| 6,548,067 B1 | 4/2003 | Seemann et al. | |
| 6,843,992 B2 | 1/2005 | Diamond | |
| 7,399,838 B2 | 7/2008 | Reiter | |
| 2003/0003535 A1 | 1/2003 | Reiter | |
| 2003/0016627 A1 | 1/2003 | McLampy et al. | |
| 2003/0017134 A1 | 1/2003 | Reiter et al. | |
| 2003/0166277 A1 | 9/2003 | Zauderer et al. | |
| 2004/0086960 A1 | 5/2004 | Reiter | |
| 2005/0063970 A1 | 3/2005 | Reiter | |
| 2009/0148925 A1 | 6/2009 | Reiter | |
| 2009/0258393 A1 | 10/2009 | Reiter | |

FOREIGN PATENT DOCUMENTS

| | | |
|---|---|---|
| JP | 02-104599 | 4/1990 |
| JP | 2003-530836 | 10/2003 |
| WO | WO 87/06261 | 10/1987 |
| WO | WO 87/06262 | 10/1987 |
| WO | WO 96/04314 | 2/1996 |
| WO | WO 97/24446 | 7/1997 |
| WO | WO 97/28191 | 8/1997 |
| WO | WO 99/14236 | 3/1999 |
| WO | WO 9928471 A2 * | 6/1999 |
| WO | WO 99/64464 | 12/1999 |
| WO | WO 01/72768 | 10/2001 |
| WO | WO 01/72768 A2 | 10/2001 |
| WO | WO 01/78768 | 10/2001 |
| WO | WO 01/78768 A3 | 10/2001 |
| WO | WO 01/90198 | 11/2001 |
| WO | WO 02/36146 | 5/2002 |
| WO | WO 02/102299 | 12/2002 |
| WO | WO 02/102840 | 12/2002 |
| WO | WO 02/102840 A2 | 12/2002 |
| WO | WO 2007/136778 | 11/2007 |

OTHER PUBLICATIONS

Mottez et al (J. Exp. Med. 1995, 181: 493-502).*
Lang et al (Cell. Molec. Life Sciences, Jun. 2002, 59(6): 1076-1080).*
Choe et al (Cancer Research 1994, 54: 3460-3467).*
Brinkmann et al (PNAS USA 1992, 89: 3075-3079).*
A_Geneseq Accession No. ABB76199 (1999).*
U.S. Appl. No. 60/801,798, filed May 19, 2006, Reiter.
Abastado, JP et al. Dimerization of Soluble Major Histocompatibility Complex-Peptide Complexes Is Sufficient For Activation of T Cell Hybridoma and Induction of Unresponsiveness. *J Exp Med.* 1995; 439-447.
Altman, JD et al. Phenotypic analysis of Antigen-specific T lymphocytes. *Science.* 1996; 274:94.

(Continued)

*Primary Examiner* — G. R. Ewoldt
*Assistant Examiner* — Marianne Dibrino

(57) ABSTRACT

This invention provides fusion proteins comprising consecutive amino acids which beginning at the amino terminus of the protein correspond to consecutive amino acids present in (i) a cytomegalovirus human MHC-restricted peptide, (ii) a first peptide linker, (iii) a human β-2 microglobulin, (iv) a second peptide linker, (v) a HLA-A2 chain of a human MHC class I molecule, (vi) a third peptide linker, (vii) a variable region from a heavy chain of a scFv fragment of an antibody, and (viii) a variable region from a light chain of such scFv fragment, wherein the consecutive amino acids which correspond to (vii) and (viii) are bound together directly by a peptide bond or by consecutive amino acids which correspond to a fourth peptide linker, wherein the antibody from which the scFv fragment is derived specifically binds to mesothelin. This invention provides nucleic acid constructs encoding same, processes for producing same, compositions, and uses thereof.

1 Claim, 18 Drawing Sheets

OTHER PUBLICATIONS

Altman, JD et al. Formation of Functional Peptide Complexes of Class II Major Histocompatibility Complex Proteins From Subunits Produced In *Escherichia coli*. *PNAS*. 1993; 10330-10334.

Bird, R et al. Single-Chain Antigen-Binding Proteins. *Science*. 1988; 242:423-426.

Bisaro, DM et al. Genetic Analysis of Tomato Golden Mosaic Virus. *Current Communications in Molecular Biology: Viral Vectors*. Guzman, Y., Editor, Cold Spring Harbor Laboratory, 1988; 172-189.

Bousso, P et al. Enrichment of Antigen-Specific T Lymphocytes By Panning On Immobilized MHC-Peptide Complexes. *Immunology Letters*. 1997; 59(2):85-91.

Brumfeld, V et al. Studies of Fibronectin and Its Domains: II Secondary Structure and Spatial Configuration of Fibronectin and Its Domains. *Arch Biochem Biophy*. 1993; 302:314.

Burrows, GG et al. Two-Domain MHC Class II Molecules Form Stable Complexes With Myelin Basic Protein 69-89 Peptide That Detect and Inhibit Rat Encephalitogenic T Cells and Treat Experimental Autoimmune Encephalomyelitis. *J Immunol*. 1998; 161:5987-5996.

Burrows, GG et al. Regulation of Encephalitogenic T Cells With Recombinant TCR Ligands. *J Immunol*. 2000; 164:6366-6371.

Davis, M et al. Ligand Recognition By Alpha Beta T Cell Receptors. *Annu Rev Immunol*. 1998; 16:523-44.

Dawson, WO et al. A Tobacco Mosaic Virus-Hybrid Expresses and Loses An Added Gene. *Virology*. 1989; 172:285-292.

Denkberg, G et al. Recombinant Human Single-Chain MHC-Peptide Complexes Made From *E. coli* By In Vitro Refolding: Functional Single-Chain MHC-Peptide Complexes And Tetramers With Tumor Associated Antigens. *Euro J Immunol*. 2000; 30 (12) :3522-3532.

DeWet et al. Exogenous gene transfer in maize (*Zea mays*) using DNA-treated pollen. In: *Experimental Manipulation of Ovule Tissue*, eds. 1985; Chapter 16:197-209.

French et al. Bacterial Gene Inserted In An Engineered RNA Virus: Efficient Expression in Monocotyledonous Plant Cells. *Science*. 1986; 231:1294-1297.

Fromm et al. Stable Transformation Of Maize After Gene Transfer By Electroporation. *Nature*. 1986; 319:791-793.

Garboczi, DN et al. HLA-A2-Peptide Complexes: Refolding and Crystallization of Molecules Expressed in *Escherichia coli* and Complexed With Single Antigenic Peptides. *PNAS*. 1992; 3429-3433.

Germain, R et al. The Biochemistry and Cell Biology of Antigen Processing and Presentation. *Ann Rev Immunol*. 1993; 11:403-450.

Gregoire, C et al. Covalent Assembly Of A Soluble T Cell Receptor-Peptide-Major Histocompatibility Class I Complex. *PNAS*, 1996; 93;7184-7189.

Hansen, TH et al. Mechanism of Class I Assembly with Beta 2 Microglobulin and Loading with Peptide. *Adv Immunol*. 1997 64:105-37.

Horsch et al. Leaf Disc Transformation. *Plant Molecular Biology Manual A5*. Kluwer Academic Publishers. Dordrecht 1988; p. 1-9.

Ignatowicz, L et al. Cells Surface Expression of Class II MHC Proteins Bound By a Single Peptide. *J Immunol*. 1995; 154:3852.

Ignatowicz, L. The Repertoire of T cells Shaped By A Single MHC/Peptide Ligand. *Cell*. 1996; 84:521.

Gatenby, AA et al. Regulation and Expression of Plant Genes in Microorganisms. J Butterworth Publishers. Boston, Mass. (1989); Chapter 5:93-112.

Kersh, GJ et al., High- And Low-Potency Ligands with Similar Affinities for the TCR: The Importance of Kinetics in TCR Signaling. *Immunity*. 1998; 9:817-826.

Klee et al. Agrobacterium-Mediated Plant Transformation and Its Further Applications to Plant Biology. *Annu. Rev. Plant Physiol*. 1987; 38:467-486.

Klee and Rogers. Plant Gene Vectors and Genetic Transformation: Plant Transformation Systems Based on the Use of *Agrobacterium tumefaciens*. In: *Cell Culture and Somatic Cell Genetics of Plants, Molecular Biology of Plant Nuclear Genes*. Academic Publishers, San Diego, Calif. 1989; 6: chapter 1:2-25.

Klein et al. Factors Influencing Gene Delivery Into *Zea mays* Cells by High-Velocity Microprojectiles. *Bio/Technology*. 1988; 6:559-563.

Kourilsky et al. Immunological Issues in Vaccine Trials: T-Cell Responses. Preclinical and Clinical Development of New Vaccines, *Dev Biol Stand*. Plotkin, SB, Brown, F and Horaud, F, eds. Basel Karger. 1998; 95:117-124.

Kozono, H et al. Production of Soluble MHC Class II Proteins With Covalently Bound Single Peptides. *Nature*. 1994; 369:151.

Lanzavecchia, A et al. From TCR Engagement to T Cell Activation: A Kinetic View of T Cell Behavior. *Cell*. 1999; 96:1.

Layton, JE et al. Identification of Ligand-Binding Site Iii on the Immunoglobulin-Like Domain of the Granulocyte Colony-Stimulating Factor Receptor. *J Biol Chem*. 2001; 276(39):36779-87.

Lee, L et al. Functional Cell Surface Expression by a Recombinant Single-Chain Class I Major Histocompatibility Complex Molecule with a Cis-Active B2-Microglobulin Domain. *Eur J Immunol*. 1994; 24:2633-2639.

Lev, A et al. Tumor-Specific Ab-Mediated Targeting of MHC-Peptide Complexes Induces Regression of Human Tumor Xenografts in Vivo. *PNAS*. 2004; 101(24):9051-9056.

Lone, et al. In Vitro Induction Of Specific Cytotoxic T. Lymphocytes Using Recombinant Single-Chain MHC Class I/Peptide Complexes. *J Immunother*. 1998; 283-294.

Low, S.C. et al. (2005) Oral and Pulmonary Delivery of FSH-Fe Fusion Proteins via Neonatal Fe Receptor-Mediated Transcytosis. *Human Reproduction*. 2005; 20(7) :1805-1813.

Marby, G et al. Engineering Therapeutic Antibody Fragments Targeting the Anthrax Toxin. Thesis: The University of Texas at Austin. 2005; pp. 1-167.

Mage, MG. et al. A Recombinant, Soluble, Single-Chain Class I Major Histocompatibility Complex Molecule with Biological Activity. *PNAS*. 1992; 89,10658-10662.

Matsumura, M. et al. In Vitro Peptide Binding To Soluble Empty Class I Major Histocompatibility Complex Molecules Isolated From Transfected Drosophila Melanogaster Cells. *J. Biol. Chem*. 1992; 267 (33) :23589-23595.

Matsumura, M et al. Emerging Principals For The Recognition Of Peptide Antigens By MHC Class I Molecules. *Science*. 1992; 257:927-34.

McCabe et al. Stable Transformation of Soybean (Glycine Max) by Particle Acceleration. *Bio/Technology*. 1988; 6:923-926.

Mottez, E et al. Cells Expressing A Major Histocompatibility Complex Class I Molecule With A Single Covalently Bound Peptide Are Highly Immunogenic. *J Exp Med*. 1995; 181:493-502.

Neuhaus and Spangenberg, Plant Transformation By Microinjection Techniques. *Physiol Plant*. 1990; 79:213-217.

Neuhaus et al. Transgenic Rapeseed Plants Obtained By the Microinjection of DNA into Microspore-Derived Embryoids. *Theor Appl Genet*. 1987; 75:30-36.

Ogg, GS et al. HLA-Peptide Tetrameric Complexes. *Curr Opin Immunol*. 1998; 10:393-396.

Ogg et al. Sensitization of Tumor Cells to Lysis By Virus-Specific CTL Using Antibody-Targeted MHC Class I/Peptide Complexes. *BJC*. 2000; 82 (5) :1058-1062.

Ohta, et al. High-Efficiency Genetic Transformation of Maize by a Mixture of Pollen and Exogenous DNA. *PNAS*. 1986; 83:715-719.

Ojcius, DM et al. Dissociation Of The Peptide-MHC Class I Complex Limits The Binding Rate Of Exogenous Peptide. *J Immunol*. 1993; 151 (11) :6020-6026.

Parker, KC et al. Peptide Binding to HLA-A2 And HLA-B27 Isolated From *Escherichia coli*. *J Biol Chem*. 1992; 267(8):5451-5459.

Parker, KC et al. Sequence Motifs Important For Peptide Binding To the Human MHC Class I Molecule, HLA-A2. *J Immunol*. 1992; 149(11):3580-3587.

Parkhurst, MR et al. Improved Induction of Melanoma-Reactive CTL with Peptides from the Melanoma Antigen GP100 Modified At HLA-A*0201-Binding Residues. *J Immunol*. 1996; 157:2539.

Paszkowski, J et al. Cell Culture and Somatic Cell Genetics of Plants. *Molecular Biology of Plant Nuclear Genes eds*. 1989; 6:52-68.

U.S. Appl. No. 60/928,915, filed Jun. 19, 2001 (Reiter, Yoram).

Paul, W.E. Structure And Function Of Immunoglobulins. *Fundamental Immunology*, 3rd Edition, 1993; 292-295.

Reiter, Y et al. Recombinant Fv Immunotoxins and FV Fragments as Novel Agents for Cancer Therapy and Diagnosis. *Trends in Biotech*. 1998; 16:513.

Retiere, C et al. Generation of Cytomegalovirus-Specific Human T-Lymphocyte Clones by Using Autologous B-Lymphoblastoid Cells with Stable Expression of pp65 or IE1 Proteins: a Tool To Study the Fine Specificity of the Antiviral Response. *J Virol*. 2000; 3948-3952.

Robert et al. Antibody-Conjugated MHC Class I Tetramers Can Target Tumor Cells For Specific Lysis By T Lymphocytes. *Euro J Immunol*. 2000; 30(11):3165-3170.

Rosenberg, SA. Cancer Vaccines Based On the Identification of Genes Encoding Cancer Regression Antigens. *Immunol Today*. 1997; 18:175.

Rudikoff et al. Single Amino Acid Substitution Altering Antigen-Binding Specificity. *PNAS*. 1982; 79:1979-1983.

Salter, RD et al. Genes Regulating HLA Class I Antigen Expression In T-B Lymphoblast Hybrids. *Immunogenetics*. 1985; 21:235.

Sanford, JC. Biolistic Plant Transformation. *Physiol. Plant*. 1990; 79:206-209.

Schagger H. Respiratory Chain Super Complexes. *IUBMB Life*. 2001; Sep.-Nov. 52(3-5):119-128.

Schatz, PJ. Use Of Peptide Libraries To Map The Substrate Specificity Of A Peptide Modifying Enzyme: A 13 Residue Consensus Peptide Specifies Biotinylation In *Escherichia coli. Biotechnology*. 1993; 11:1138.

Siniossoglou S. et al. Structure and Assembly of the Nup84p Complex. *J Cell Bio*. 2000; 149:41-53.

Stern, LJ et al. The Human Class II MHC Protein HLA-DR1 Assembles As Empty Heterodimers In The Absence Of Antigenic Peptide. *Cell*. 1992; 68:465.

Sylvester-Hvid, C. et al. A Single-Chain Fusion Molecule Consisting Of Peptide, Major Histocompatibility Gene Complex Class I Heavy Chain And Beta2-Microglobulin Can Fold Partially Correctly, But Binds Peptide Inefficiently. Scand J Immunol. 1999; 50:355-362.

Tafuro, S et al. Reconstitution of Antigen Presentation in HLA Class I-Negative Cancer Cells with Peptide-Beta2m Fusion Molecules. *Euro J Immunol*. 2001; 31:440-449.

Takamatsu et al. Expression of Bacterial Chloramphenicol Acetyltransferase Gene in Tobacco Plants Mediated By TMV-RNA. *EMBO J*. 1987; 6:307-311.

Takamatsu et al. Production Of Enkephalin In Tobacco Protoplasts Using Tobacco Mosaic Virus RNA Vector. *FEBS Letters*. 1990; 269:73-76.

Toriyama, K et al. Transgenic Rice Plants After Direct Gene Transfer Into Protoplasts. *Bio/Technology*. 1988; 6:1072-1074.

Toshitani, K et al. Expression Of Single-Chain HLA Class I Molecule In A Human Cell Line: Presentation Of Exogenous Peptide And Processed Antigen To Cytotoxic T Lymphocytes. *PNAS*. 1996; 93:236-240.

Uger, RA et al. Creating CTL Targets with Epitope-linked 2-Microglobulin Constructs. *J Immunol*. 1998; 160:1598.

Valitutti, S et al. Serial Triggering Of Many T-Cell Receptors By A Few Peptide-MHC Complexes. *Nature*. 1995; 375:148.

Van den Eynde, B et al. T-cell-Defined Tumor Antigens. *Curr Opin Immunol*. 1997; 9:684.

White, J et al. Soluble Class I MHC With B2-Microglobulin Covalently Linked Peptides: Specific Binding To A T Cell Hybridoma. *J Immunol*. 1999; 162:2671-2676.

Zajac, P. et al. Generation Of Tumoricidal Cytotoxic T Lymphocytes From Healthy Donors After In Vitro Stimulation With A Replication-Incompetent Vaccinia Virus Endocing MART-1/MELAN-A 27-35 Epitope. *Int J Cancer*. 1997; 71:491-496.

Zhang et al. Transgenic Rice Plants Produced By Electroporation-Mediated Plasmid Uptake into Protoplasts. *Plant Cell Rep*. 1988; 7:379-384.

International Preliminary Report on Patentability Dated Dec. 4, 2008 From the International Bureau of WIPO Re. Application No. PCT/US2007/011953.

International Search Report Dated Dec. 12, 2007 From the International Searching Authority Re. Application No. PCT/US07/11953.

Lev et al. "Tumor-Specific Ab-Mediated Targeting of MHC-Peptide Complexes Induces Regression of human Tumor Xenografts In Vivo", Proc. Natl. Acad. Sci. USA, PNAS, 101(24): 9051-9056, Jun. 15, 2004. Abstract, P.9051, col. 1, § 1, col. 2, § 1, 2, 4, p. 9052, Fig.1B, col. 1, § 3, col. 2, § 3, p. 9055, col. 1, § 2, p. 9056, col. 2, § 2.

Low et al. "Oral and Pulmonary Delivery of FSH-Fc Fusion Proteins Via Neonatal Fc Receptor-Mediated Transcytosis", Human Reproduction, 20(7): 1805-1813, 2005. p. 1806, col. 1, § 9.

Mabry III "Engineering Therapeutic Antibody Fragments Targeting the Anthrax Toxin", Dissertation, Presented to the Faculty of the Graduate School of The University of Texas at Austin for the Degree of Doctor of Philosophy, 182 P., Aug. 2005. p. 75, Fig.3.1.

Retière et al. "Generation of Cytomegalovirus-Specific Human T-Lymphocyte Clones by Using Autologous B-Lymphoblastoid Cells With Stable Expression of PP65 or IE1 Proteins: A Tool to Study the Fine Specificity of the Antiviral Response", Journal of Virology, 74(9): 3948-3952, May 2000.

Official Action Dated Oct. 11, 2010 from the Eurasian Patent Office Re. Application No. 200870555/28 and Its Translation into English.

Mage et al. "A Recombinant, Soluble, Single-Chain Class 1 Major Histocompatibility Complex Molecule with Biological Activity", PNAS, 89: 10658-10662, 1992.

Communication Pursuant to Article 94(3) EPC Dated Dec. 1, 2009 From the European Patent Office Re. Application No. 07777164.0.

Communication Pursuant to Rules 161 and 162 EPC Dated Jan. 20, 2009 From the European Patent Office Re. Application No. 07777164.0.

Response Dated Mar. 12, 2010 to Communication Pursuant to Article 94(3) EPC of Dec. 1, 2009 From the European Patent Office Re. Application No. 07777164.0.

Supplementary European Search Report and the European Search Opinion Dated Aug. 24, 2009 From the European Patent Office Re. Application No. 07777164.0.

Hassan et al. "Mesothelin: A New Target for Immunotherapy", Clinical Cancer Research, XP009076012, 10(12/Pt.01): 3937-3942, Jun. 15, 2004.

Oved et al. "Antibody-Mediated Targeting of Human Single-Chain Class I MHC With Covalently Linked Peptides Induces Efficient Killing of Tumor Cells by Tumor or Viral-Specific Cytotoxic T Lymphocytes", Cancer Immunology, XP019333169, 54(9): 867-879, Sep. 1, 2005.

International Preliminary Examination Report Dated Sep. 3, 2004 From the International Preliminary Examining Authority Re.: Application No. PCT/IL02/00478.

Communication Pursuant to Article 94(3) EPC Dated Dec. 2, 2009 From the European Patent Office Re. Application No. 02733206.3.

Communication Pursuant to Article 96(2) EPC Dated Aug. 6, 2007 From the European Patent Office Re. Application No. 02733206.3.

Examination Report Dated Jun. 9, 2008 From the Intellectual Property Office of New Zealand Re. Application No. 568650.

Examination Report Dated Dec. 14, 2009 From the Intellectual Property Office of New Zealand Re. Application No. 581793.

Examination Report Dated May 23, 2005 From the Intellectual Property Office of New Zealand Re. Applicaiton No. 530656.

Examination Report Dated Feb. 24, 2010 From the Intellectual Property Office of New Zealand Re. Application No. 581793.

Examination Report Dated Nov. 29, 2006 From the Intellectual Property Office of New Zealand Re. Applicaiton No. 530656.

Examination Report Dated Nov. 29, 2006 From the Intellectual Property Office of New Zealand Re. Application No. 551473.

Examiner's Report Dated Feb. 19, 2007 From the Australian Government, IP Australia Re. Application No. 2002304279.

Examiner's Report Dated Aug. 27, 2010 From the Australian Government, IP Australia Re. Application No. 2008243241.

Notification Dated Jul. 1, 2010 From the Polish Patent Office Re. Application No. P-373302 and Its Translation Into English.

Office Action Dated Sep. 7, 2010 From the Israel Patent Office Re. Application No. 160412 and Its Translation Into English.

Official Action Dated May 5, 2010 From the US Patent and Trademark Office Re. U.S. Appl. No. 10/482,532.

Official Action Dated Apr. 17, 2008 From the US Patent and Trademark Office Re. U.S. Appl. No. 10/482,532.

Official Action Dated Mar. 20, 2007 From the US Patent and Trademark Office Re. U.S. Appl. No. 10/482,532.

Official Action Dated Jul. 23, 2009 From the US Patent and Trademark Office Re. U.S. Appl. No. 10/482,532.

Official Action Dated Jul. 27, 2007 From the US Patent and Trademark Office Re. U.S. Appl. No. 10/482,532.

Response Dated Feb. 12, 2010 to Examination Report of Dec. 14, 2009 From the Intellectual Property Office of New Zealand Re. Application No. 581793.
Response Dated Apr. 13, 2010 to Communication Pursuant to Article 94(3) EPC of Dec. 2, 2009 From the European Patent Office Re. Application No. 02733206.3.
Response Dated Apr. 20, 2007 to Official Action of Mar. 20, 2007 From the US Patent and Trademark Office Re. U.S. Appl. No. 10/482,532.
Response Dated May 20, 2009 to Official Action of Apr. 17, 2008 From the US Patent and Trademark Office Re. U.S. Appl. No. 10/482,532.
Response Dated Jun. 21, 2010 to Examination Report of Feb. 24, 2010 From the Intellectual Property Office of New Zealand Re. Application No. 581793.
Response Dated Jan. 25, 2010 to Official Action of Jul. 23, 2009 From the US Patent and Trademark Office Re. U.S. Appl. No. 10/482,532.
Response Dated Jan. 28, 2008 to Official Action of Jul. 27, 2007 From the US Patent and Trademark Office Re. U.S. Appl. No. 10/482,532.
Response Dated May 28, 2008 to Examination Report of Nov. 29, 2006 From the Intellectual Property Office of New Zealand Re. Application No. 551473.
Supplementary European Search Report Dated Apr. 3, 2007 From the European Patent Office Re. Application No. 02733206.3.
Translation of Decision of Rejection Dated Nov. 17, 2009 From the Japanese Patent Office Re. Application No. 2003-504888.
Translation of Final Notice of Rejection Dated Apr. 14, 2009 From the Japanese Patent Office Re. Application No. 2003-504888.
Translation of Notice of Reasons for Rejection Dated Aug. 5, 2008 From the Japanese Patent Office Re. Application No. 2003-504888.
Bird et al. "Single-Chain Antigen-Binding Proteins", Science, 242: 423-426, Oct. 21, 1988.
Godeau et al. "Organization of Phosphatidylcholine and Sphingomyelin in the Surface Monolayer of Low Density Lipoprotein and Lipoprotein(a) as Determined by Time-Resolved Fluorometry", The Journal of Biological Chemistry, 267(34): 24223-24229, Dec. 5, 1992.
Godeau et al. "Purification and Ligand Binding of A Soluble Class I Major Histocompatibility Complex Molecule Consisting of the First Three Domains of H-2Kd Fused to β2-Microglobulin Expressed in the Baculovirus-Insect Cell System", The Journal of Biological Chemistry, 267(34): 24224-24229, Dec. 5, 1992.
Hicklin et al. "HLA Class I Antigen Downregulation in Human Cancers: T-Cell Immunotherapy Revives An Old Story", Molecular Medicine Today, 5: 178-186, Apr. 1999.
Ogg et al. "Sensitization of Tumour Cells to Lysis by Virus-Specific CTL Using Antibody-Targeted MHC Class I/Peptide Complexes", British Journal of Cancer, 82(5): 1058-1062, 2000.
Riddell et al. "Class I MHC-Restricted Cytotoxic T Lymphocyte Recognition of Cells Infected With Human Cytomegalovirus Does Not Require Endogenous Viral Gene Expression", The Journal of Immunology, 146(8): 2795-2804, Apr. 15, 1991. Abstract.
Robert et al. "Antibody-Conjugated MHC Class I Tetramers Can Target Tumor Cells for Specific Lysis by T Lymphocytes", European Journal of Immunology, XP001021944, 30(11): 3165-3170, Nov. 2000. Abstract, P.3168, r-h Col.
Uger et al. "Creating CTL Targets With Epitope-Linked Beta 2-Microglobulin Constructs", Journal of Immunology, XP002115504, 160(4): 1598-1605, Feb. 15, 1998.
Communication Pursuant to Article 94(3) EPC Dated Mar. 11, 2009 From the European Patent Office Re.: Application No. 01914159.7.
Examiner's Report Dated Feb. 18, 2010 From the Australian Government, IP Australia Re.: Application No. 2007203607.
International Preliminary Examination Report Dated May 20, 2005 From the International Preliminary Examining Authority Re.: Application No. PCT/IL01/00260.
International Search Report Dated Oct. 17, 2002 From the International Searching Authority Re.: Application No. PCT/IL01/00260.
Interview Summary and Supplemental Response Dated Dec. 23, 2010 to Telephone Interview With Examiner on Dec. 21, 2010 in the US Patent and Trademark Office Re. U.S. Appl. No. 10/482,532.
Official Action Dated Jan. 4, 2011 From the US Patent and Trademark Office Re. U.S. Appl. No. 10/482,532.

Official Action Dated Apr. 5, 2007 From the US Patent and Trademark Office Re.: U.S. Appl. No. 10/073,300.
Official Action Dated Oct. 6, 2006 From the US Patent and Trademark Office Re.: U.S. Appl. No. 10/073,300.
Official Action Dated Apr. 8, 2005 From the US Patent and Trademark Office Re.: U.S. Appl. No. 10/073,300.
Official Action Dated Apr. 10, 2006 From the US Patent and Trademark Office Re.: U.S. Appl. No. 10/075,257.
Official Action Dated Jan. 11, 2007 From the US Patent and Trademark Office Re.: U.S. Appl. No. 10/075,257.
Official Action Dated Mar. 16, 2006 From the United State Patent and Trademark Office Re.: U.S. Appl. No. 10/073,300.
Official Action Dated Dec. 18, 2008 From the US Patent and Trademark Office Re.: U.S. Appl. No. 10/075,257.
Official Action Dated Mar. 18, 2008 From the United States Patent and Trademark Office Re.: U.S. Appl. No. 10/075,257.
Official Action Dated Sep. 19, 2007 From the US Patent and Trademark Office Re.: U.S. Appl. No. 10/073,300.
Official Action Dated Oct. 24, 2005 From the US Patent and Trademark Office Re.: U.S. Appl. No. 10/075,257.
Official Action Dated Feb. 25, 2005 From the US Patent and Trademark Office Re.: U.S. Appl. No. 10/075,257.
Altman et al. "Formation of Functional Peptide Complexes of Class II Major Histocompatibility Complex Proteins From Subunits Produced in *Escherichia coli*", Proc. Nat. Acad. Sci. USA, 90: 10330-10334, 1993.
Berko et al. "Membrane-Anchored Beta2-Microglobulin Stabilizes a Highly Receptive State of MHC Class I Molecules", The Journal of Immunology 174: 2116-2123, 2005.
Bousso et al. "Enrichment of Antigen-Specific T Lymphocytes by Panning on Immobilized MHC-Peptide Complexes", Immunology Letters, 59(2): 85-91, 1997. Abstract. p. 86, col. 1.
Denkberg et al. "Recombinant Human Single-Chain MHC-Peptide Complexes Made From *E. coli* by In Vitro Refolding: Functional Single-Chain MHC-Peptide Complexes and Tetramers With Tumor Associated Antigens", European Journal of Immunology, 30(12): 3522-3532, 2000. Abstract. p. 3524, col. 1, § 2, From Bottom.
Fan et al. "Direct Binding of A Soluble Natural Killer Cell Inhibitory Receptor to A Soluble Human Leukocyte Antigen-Cw4 Class I Major Histocompatibility Complex Molecule", Proc. Natl. Acad. Sci. USA, 93(14): 7178-7183, Jul. 1996.
Garboczi et al. "HLA-A2-Peptide Complexes: Refolding and Crystallization of Molecules Expressed in *Escherichia coli* and Complexed With Single Antigenic Peptides", Proc. Natl. Acad. Sci. USA, 89: 3429-3433, 1992. Abstract. p. 3429, col. 1, § 1.
Gregoire et al. "Covalent Assembly of A Soluble T Cell Receptor-Peptide-Major Histocompatibility Class I Complex", Proc. Natl. Acad. Sci. USA, 93: 7184-7189, Jul. 1996.
Kourilsky et al. "Immunological Issues in Vaccine Trials: T-Cell Responses", Preclinical and Clinical Development of New Vaccines, 95: 117-124, 1998.
Lee et al. "A Recombinant Single-Chain HLA-A2.1 Molecule, With A Cis Active b2-Microglobulin Domain, Is Biologically Active in Peptide Binding and Antigen Presentation", Human Immunology, 49(1): 28-37, 1996.
Lee et al. "Functional Cell Surface Expression by A Recombinant Single-Chain Class I Major Histocompatibility Complex Molecule With A Cis-Active Beta 2-Microglobulin Domain", European Journal of Immunology, 24(11): 2633-2639, 1994.
Lone et al. "In Vitro Induction of Specific Cytotoxic T Lymphocytes Using Recombinant Single-Chain MHC Class I/Peptide Complexes", Journal of Immunotherapy, 21(4): 283-94, 1998.
Mage et al "A Recombinant, Soluble, Single-Chain Class 1 Major Histocompatibility Complex Molecule with Biological Activity", PNAS, 89: 10658-10662, 1992.
Matsumura et al. "In Vitro Peptide Binding to Soluble Empty Class I Major Histocompatibility Complex Molecules Isolated From Transfected Drososphila Melanogaster Cells", Journal of Biological Chemistry, 267(33): 23589-23595, 1992.
Mottez et al. "Cells Expressing A Major Histocompatibility Complex Class I Molecule With A Single Covalently Bound Peptide Are Highly Immunogenic", Journal of Experimental Medicine, 181(2): 493-502, 1995. Abstract. p. 493, col. 2, p. 495, Fig. 1.

Ogg et al. "HLA-Peptide Tetrameric Complexes", Current Opinion in Immunology, 10: 393-396, 1998.

Ojcius et al. "Dissociation of the Peptide-MHC Class I Complex Limits the Binding Rate of Exogenous Peptide", Journal of Immunology, 151(11): 6020-6026, 1993.

Parker et al. "Peptide Binding to HLA-A2 and HLA-B27 Isolated From *Eschericia coli*", The Journal of Biological Chemistry, 267(8): 5451-5459, 1992.

Parker et al. "Sequence Motifs Important for Peptide Binding to the Human MHC Class I Molecule, HLA-A2", Journal of Immunology, 149(11): 3580-3587, 1992.

Patamawenu et al. "Generation of Functional HLA-A2 Molecules Covalently Attached to Antigenic Peptides", Thesis (Master of Science in Biomedical Science), University of Maryland, 1988. Abstract.

Rammensee et al. "MHC Molecules as Peptide Receptors", Current Opinion Immunology, 5(1): 35-44, 1993.

Rotzschke et al. "Isolation and Analysis of Naturally Processed Viral Peptides as Recognized by Cytotoxic T Cells", Nature, 384: 252-254, 1990.

Shields et al. "Characterization of the Interactions Between MHC Class I Subunits: A Systematic Approach for the Engineering of Higher Affinity Variants of Beta2-Microglobulin", The Journal of Imunology, 160: 2297-2307, 1998.

Sylvester-Hvid et al. "A Single-Chain Fusion Molecule Consisting of Peptide, Major Histocompatibility Gene Complex Class I Heavy Chain and b2-Microglobulin Can Fold Partially Correctly, But Binds Peptide Inefficiently", Scandinavian Journal of Immunology, 50(4): 355-352, 1999. p. 358, col. 1, Fig. 2, p. 358, col. 2, ff, p. 357, col. 1, § 1.

Tafuro et al. "Reconstitution of Antigen Presentation in HLA Class I-Negative Cancer Cells With Peptide-b2M Fusion Molecules", European Journal of Immunology, 31(2): 440-449, 2001. Abstract. p. 442, Fig. 1.

Toshitani et al. "Expression of A Single-Chain HLA Class I Molecule in A Human Cell Line: Presentation of Exogenous Peptide and Processed Antigen to Cytotoxic T Lymphocytes", Proc. Natl. Acad. Sci. USA, 93(1): 236-240, 1996. Abstract, p. 237, col. 2, Last §, Fig. 1, p. 236, col. 2, p. 237, col. 2, § 2 From the Bottom, p. 240, §1.

Uger et al "Covalent Linkage to b2-Microglobulin Enhances the MHC Stability and Antigeniticity of Suboptimal CTL Epitopes", The Journal of Immunology, 162: 6024-6028, 1999.

Urban et al. "The Discovery and Use of HLA-Associated Epitopes as Drugs", Critical Reviews in Immunology, 17(5-6): 387-397, 1997.

Zajac et al. "Generation of Tumoricidal Cytotoxic T Lymphocytes From Healthy Donors, After In-Vitro Stimulation With A Replicatin-Incompetent Vaccina Virus Encoding Mart-1/Melan-A 27-35 Epitope", International Journal of Cancer, 71: 491-496, 1997.

Communication Pursuant to Article 94(3) EPC Dated Mar. 24, 2011 From the European Patent Office Re. Application No. 07777164.0.

European Search Report and the European Search Opinion Dated Mar. 16, 2011 From the European Patent Office Re. Application No. 10166544.6.

Response Dated Mar. 20, 2011 to Office Action of Jan. 27, 2011 From the Patent Office of the State Intellectual Property Office of the People's Republic of China Re. Application No. 200780018196.5.

Response Dated Apr. 4, 2011 to Official Action of Jan. 4, 2011 From the US Patent and Trademark Office Re. U.S. Appl. No. 10/482,532.

Translation of Official Decision for Rejection Dated Apr. 15, 2011 From the Japanese Patent Office Re. Application No. 2001-571699.

Burrows et al. "Two-Domain MHC Class II Molecules Form Stable Complexes With Myelin Basic Protein 69-89 Peptide That Detect and Inhibit Rat Encephalitogenic T Cells and Treat Experimental Autoimmune Encephalomyelitis", The Journal of Immunology, 161: 5987-5996, 1998.

* cited by examiner

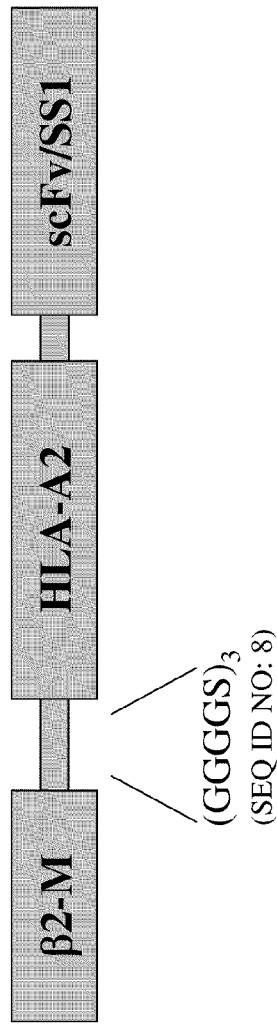
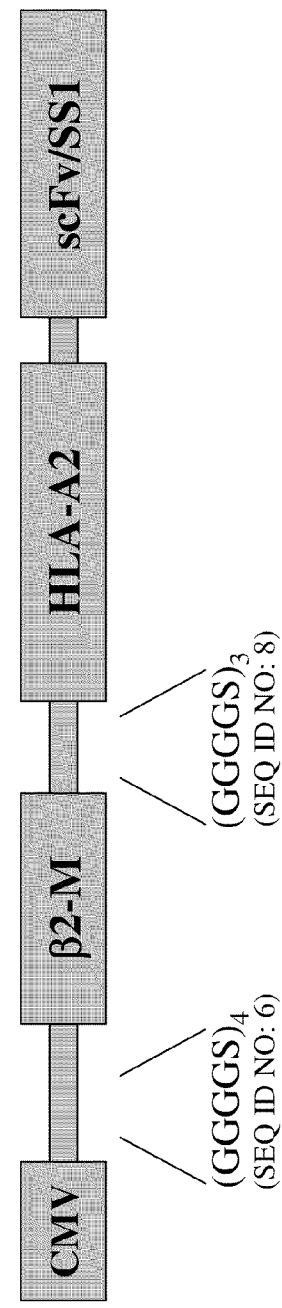
Fig 1

Fig 2

ATGAACCTGGTGCCGATGGTCGGAGACCGTTGGAGGTGGGCGGTTCTGGCGGAGGAGGATCCGGTGGCGGA
GGTTCAGGAGGCGGTGGATCGATCCAGCGTCCAAAGATTCAGGTTTACTCACGTCATCCAGCAGAGAA
TGGAAAGTCAAATTCCTGATTGCTATGTGTCTGGGTTTCATCCGACATTGAAGTTGACTTACTGAAG
AATGGAGAGAGAATTGAAAAAGTGGAGCATTCAGACTGTCTTTCTGTTCTCTATCTCTTGT
ACTACACTGAATTCACCCCACTGAAAAAGATGAGTATGCCGTGTGAACCATGTGACTTTGTCACAGC
CCAAGATAGTTAAGTGGGATCGCGACATGGGTGCGCGGCGCGGTGGAAGCGCGGTGGAAGGTG
GCAGCGGCTCTCACTCCATGGCTATTTCTTCACATCCGTGTCCGGCCCGGCCGCGGGAGCCCGCTT
CATCGCAGTGGGCTACGTGGACGACACGCAGTCGTGCGGTTCGACGCGACGCCGCAGAGGAT
GGAGCCGCGGCCGTGGATAGAGCAGGAGGTCCGGAGTATTGGGACGGGGAGACACGGAAAGTGA
AGGCCCACTCACAGACTCACCGAGTGGAACCTGGGGACCCTGCCGGCTACTACAACCAGAGCGAGGCCG
GTTCTCACACCGTCCAGAGACGATGTATGGCTGCGACGTGGGGTCGGACTGGCGCTTCCTCCGCGGGTACCA
CCAGTACGCGTACGACGGCAAGGATTACATCGCCCTGAAAGAGACCTGCGCTCTTGGACCGGCGGGAC
ATGGCAGCTCAGACGACCACCAAGCACACAAGTGGGAGGCGGCCCATGTGAGAGCGGAAGAAGGGGAGACGCGCAGCGCAGCTACCTGG
AGGGCACGTGCGAGTGCGCCGAGTACCTGGAGAACGGAAGAGCGAAGCCACCCTGAGGTGCTGGGCCTGAG
CCCCCAAAACGCACATGACTCGTCTCTGACCATGAAGCACCTGAGGTGCCAGGACCAGGACACGGAGCTC
CTTCTACCCTGCGGAGATCACACTGACCTGGCAGCGGGATGGGGAGGACCCAGGACGCTGTGGTGCCTTCTGGACAG
GTGGAGACAAGGCCTGCAGGGGATGGAAGCCTTGCAGCCAGGGTTTGCCCAAGCACCCCCTGAGATGGGGAGTC
GAGCAGAGATACACCTCAGGAGCCCAGTGCAGCAGTCACTGGCTACAACTGGGCCTGGAGAAGCCTGAAGATATC
CGGAGTCAGGGCTTCTGGTTACTCATTACTCCTTACAATGTGCTTCTAGCTACAACCAGAAGTTCAGATCTGCAG
CTGCAAGGCTTCTGGTGGATTGGACTTATGTAGACAAGTCATCCAGCAGCCTACATGGACCTCCTCAGTCTGCAG
TTGAGTGGATTGGACTTGTAGACAAGTCATCCAGCAGCCTACATGGACCTCCTCAGTCTGACATCTGCAG
CATTAACTGTAGACAAGTCATCCAGCAGCCTACATGGACCTCCTCAGTCTGACACCAGCCACCGGTCAC
TCTATTTCTGTGCAAGGTGTACGACGGAGGGTTTGACTACTGGGGCCAAGGACCACCGGTCAC
CGTCTCCTCAGGTGTAGCGGGTTCAGCGCGCGGTGGCCTCGGCGCGGTGGCGGATCGGACATGGACTCAC
TCAGTCTCCAGCAATCATGTCTGCATCTCCAGGGAGAAGGTCACCATGACCTGCAGTGCCAGTCAAGTG
TAAGTTACATGCACTGGTACCAGCAGAAGTCAGGCACCTCCCCAAAAGATGGATTTATGACACATCCAAAAC
TGGCTTCTGGAGTCCCAGCTCGCTTCAGTGGCAGTGGGTCTGGGAAACTTCTCTCTCACAATCAGCAGC
GTGGAGGCTGAAGATGATGCAACTTATTACTGCCAGCAGTGGAGTAAGCACCCTCACGTTCGGTGCTGG
GACAAAGTTGGAAATAAATAATGA

A. pep/scHLA-A2/SS1(scFv)

Fig 8

```
5'ATGAACCTGGTCGCCGATGGTCGGCGACCGTTGCCGGAGGAGGATCCCGTGGCGGAGGTTCAGGAGGCGGTGGATCG
ATCCAGCGTACTCCAAAGATTCAGGTTTACTCACGTCATCCAGCAGAATGAAAGTCAAATTTCCTGAATTGCTATGT
GTCTGGGTTTCATCCATCCGACATTGAGTTGACTTACTGAAGAGAATGGAGAGAGAATTGAAAAGTGGAGCATTCAGAC
TTGTCTTTTTCGAAGGACTGGTCTTTCTATCTCTTGTACTACACTCACCCCACTGAAAAAGATGAGTATGCCTG
CCGTGTGAACCATGTGACTTTGTCACAGCCCAAGATAGTTAAGTGGGATCGCGACATGGGTGGCGGTGGAAGCGGCG
GTGGAGGCGCTCTGTGGCAGCGGGGCTCTCCATGAGGTATTTCTTCACATCCGTGTCCCGGCCGC
GGGGAGCCCCGCTTCATCGCAGTGGGCTACGTGGACGACACGCAGTTCGTGCGGTTCGACAGCGACGCGGGAGCC
AGAGGATGGAGCGCGCCGTGAGTGGACCAGGAGGGTCCGGAGTATTGGGACGGGGAGACACGGAAAGTGAA
GGCCCACTCACAGACTCACCGAGTGGGACCCTGCGCGGCCTACTACACCAGAGCGGAGGCGGTTCTCACA
CCGTCCAGAGGATGTATGCGCCCTGCGACGTCGGACTGGGCTTCCTCCGCGGGGGACATGGCAGCTCAGACCACCAAGCA
GGCAAGGATTACATCGCCCTGAAAGAGGACCTGCGTTGAGAGCGTAGCGGAGCAGTGGGGCACGTGCGTGGCTCCGGCAGA
CAAGTGGGAGGCCCATGCGCGTGGGCGGGGCGTGCAGCGGACGCTGCAGCGCGACGCCCCAAAACGCACATCACAACTGACCCTGTCTCTGA
TACCTGGAGAACGGGAAGGCCACCCTGAGGTGCTGGGCCCTGAGCTTCTACCCTGCGGAGATCACACCTGGCAGCGGGATGGGG
CCATGAAGCCACCCTGAGGTGCTGGGCCCTGAGCTTCTACCCTGCGGAGATCACACCTGGCAGCGGGATGGGG
AGGACCAGGACACCAGGACACGGAGCTCGTGCAGCAGATACACCTGCCATGTGCAGCATGAGGGTTGCCCAAGCCCCTCACCCTGA
GGTGGTGCCTTCTGGAGGAGCCAGAGTACAACTGCAGGTCAGTCTGGGCCTGAGCTGGGTGAAGAGCCTTG
GATGGGAGCTTCCGAGCTCCGAGGTCAGGTACTCATTCTGGTTACTACTCCTTACAATGGTGCTTCTAGCTAGCAACCCAGAAGTTCAGGGCAGGGCAAGGCCACATTAACTGT
ATATCCTGCAAGGCTTCTGGTTACTCATTCACCCGCTACACCGCAAATGGTGCTTCTAGCTAGCAACCCAGAAGTTCAGGGCAGGGCAAGGCCACATTAACTGT
AGTTGGATTGGACTTATTACTTCCTTACAATGGTGCTTCTGGAGCACATTATCCGGCAGAGCCGGAGACATCTGAAGACTCTGAAGACTCTGAGACTCTGCAAGG
AGACAAGTCATCCAGCACACTACATGGAGACCCTCAGTCTGACATCTGAAGACTCTGAAGACTCTGAAGACTCTGAAGACTCTGAAGACTCTGCATCTCCTGCAAGG
GGGGGTTACGACGGGAGGGGTTTGACTACTGGGGACCCAAGGCCAGCTCAGCTCACTCAGTCTCCAGCAATCATGTCTGCATCTCCAG
AGCGGCGGCGTGGCTTCCGAGGTCCGGGATCGGACATCGAGCTCGAGCTGGACATCGTGAGCTGTAAGTTACATGCAGCAGAAGTCAGGCACCT
GGGAGAAGGTCACCATGACCTGCAGTGCCAGTCAAGTTACATGCAGCAGAAGTCAGGCACCT
CCCCAAAGATGGATTTATGACACATCCAGCACTACTGGCTTCTGGAGTCCCAGGTCCGCTTCAGTGGCAGTGGGTCTGGAA
ACTCTTACTCTCTCACAATCAGCAGCGTGAAGGCTGAAGATGATGCAACTTATTACTGCCAGCAGTGGAGTAAGCACCC
TCTCACGTTCGGTGCTGGGACAAAGTTGGAAATAAATGA3'
```

Fig 13
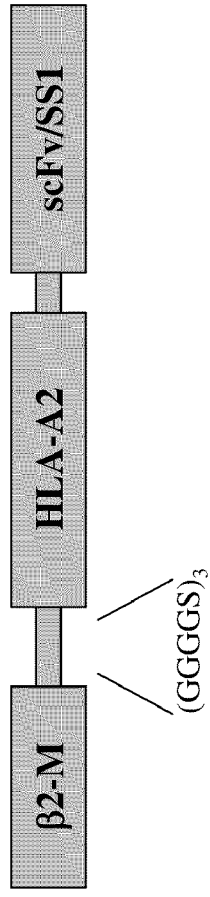
A. scHLA-A2/SS1(scFv)
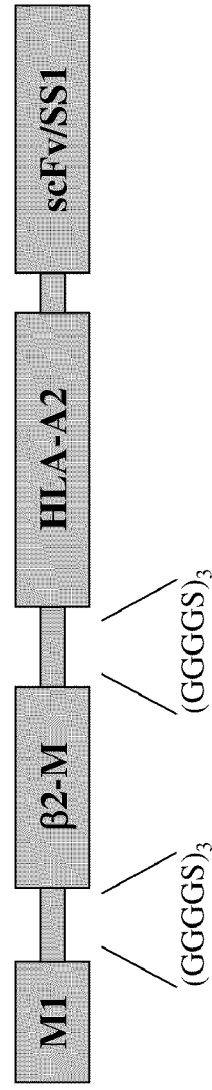
B. M1/scHLA-A2/SS1(scFv)

Fig 14

```
ATGGGCATTCTGGGCTTCGTGTTTACCCTGGCGCGAGGAGGATCCGGTGCGGCGAGGTCAGGCACGCGGTGG
ATCGATCCAGCGTACTCCAAAGATTCAGGTTACTCAGTCATCCAGCAGAGAATGGAAAGTCAAATTCCTGA
ATTGCTATGTCTGGGTTTCATCCGACATTGACTTACTGAAGAAGAATGGAGAGAGAATTGAAAAA
GTGGAGCATTCAGACTTGTCTTTTCGAAGGACTGGTCTTCTATCTCTTGTACTACACTGAATTCACCCCAC
TGAAAAAGATGAGTATGCCTGCCGTGTGAACCATGTGACTTTGTCACAGCCCAAGATAGTTAAGTGGGATCGC
GACATGGGTGCGGGTGGAAGCGGCGGGTGGAGGCTCTGGAGGCTGCAGGTCGCAGTGGGCTACGTGGACGAC
ATTTCTTCACATCCGTGTCCCGGCCCGGCGACGCGCCGGAGCCCGCTTCATCGCAGTGGGCTACGTGGACGAC
ACGCAGTTCGTGCGGTTCGACAGCGACGGCGACGGGCGAGCCCAGAGGATGGAGCCGCGTGGGATAGAGC
AGGAGGGTCCGGAGTATTGGACGGGGAGACACGGAGGCGAAGGCCCACTCACAGACTCACCGAGTGGAC
CTGGGACCCTGCGCGGCTACTACAACCAGAGCGAGGCCGGTTCTCACACCGTCCAGAGGATGTATGGCTG
CGACGTGGGGTCGGACTGGCGCTTCCTCCGCGGGTACCACCAGTGGCCGTACGACGGCAAGATTACATCG
CCCTGAAAGAGGAACCTGCGCTCTGCTTGGACCGGGGCGAGCAGCTCAGACGCAGTCAGACCACCAAGCACCAAGTGGGAG
GCGGCCCATGTAGCGGGAGCAGTGAGACGCTGCAGCGCACCGAGGGCACGTGCGTGGAGTGGCTCCGCAGATACCT
GGAGAACGGGGAAGGAGAGACGCCACCCTGAGGTGCTGCAGGCCCTGAGCTGCCCAAAACGCACATGACTCACCACCGCTGTCTCTG
ACCATGAAGCACCCTGAGGTGCTGGGCCCTGAGCTTCTACCCTGCGGAAATCACACTGACCTGGCAGCGG
GATGGGGAGGACCAGACCAGAGCACGGAGACCAGGAGCTCGTGGAGACCAGGCCTGCAGGGGATGGAACCTTCCAGAA
GTGGCGGCTGTGGTGGCTGCCTTCTGGACAGGAGCAGAGATACACCTGCCATGTGCAGCATGAGGGTTGC
CCAAGCCCCTCACCCTGAGATGGGAGGGTCGGGAGGTCAGGTGTACACCTGCCATGAGAGCAGTCTGGGCCTGAGCTG
GAGAAGCCTGCCGCTTCAGTGAAGATATCCTGCAAGGCTTCTGGTTACTCATTCATTCACTGCTACACCATGAACT
GGGTGAAGCAGAGACCATGGAAAGAGCCTTGAGTGAGATTGGAACAAGCCTACACAGCCTACATGGACCTCCTC
CAACCAGAAGTTCAGGGGCAAGGACTCTGCAGTCTGCAGTCTATTTCTGTCAAGGGGGTTACGACGGAGGGTTTGACTACT
AGTCTGACATCTGAAGACTCTGCAGTCTGCAGTCTATTTCTGTGCAAGGGGGTTACGACGGAGGGTTTGACTACT
GGGGCCAAGGGACCACGGTCACCGTCTCACAGGTGTAGGGGGTTCAGGGGGTGGGTCTGGGGTGG
CGGATCGGACATCGGAGCTCACTCAGTCTCCAGCAATCATGTCTGCATCTCCAGGGGAGAAGGTCACCATGAC
CTGCAGTGCCAGCTCAAGTAAGTTACATGCACTGTAAGTTACACTGGTACCAGCAGAAGTCAGGCACCTCCCCAAAGATG
GATTTATGACACATCCAAACTGGCTTCTGGAGTCCCAGGTCGCTTCAGTGGCAGTGGGTCTGGAAACTCTTAC
TCTCTCACAATCAGCAGCGTGGAGGCTGAAGATGCGAACTTATTACTGCCAGCAGTGGAGTAAGCACCCTC
TCACGTTCGGTGCTGGGACAAAGTTGGAAATAAATGA
```

FUSION PROTEINS, USES THEREOF AND PROCESSES FOR PRODUCING SAME

This application claims benefit of U.S. Provisional Application No. 60/801,798, filed May 19, 2006, the contents of which are hereby incorporated by reference into this application.

BACKGROUND OF THE INVENTION

Throughout this application, certain publications are referenced. Full citations for these publications may be found immediately preceding the claims. The disclosures of these publications are hereby incorporated by reference into this application in order to more fully describe the state of the art to which this invention relates.

According to current immune surveillance theory, the immune system continuously locates and destroys transformed cells. However, some cells escape from an apparently effective immune response and consequently become tumors (1-4). Tumor evasion from immune response is a well established phenomenon demonstrated in numerous studies and is caused by a wide variety of suggested mechanisms (1-4). Among these mechanisms are: the production of suppressive cytokines, the loss of immunodominant peptides, the resistance to killing mechanisms (apoptosis), and the loss of MHC class I (1-4). One of the evasion mechanisms shown to be strongly correlated with tumor progression is the loss or down regulation of MHC class I molecules. This evasion mechanism is abundant in many tumors and can result from a number of different mutations. Several studies revealed weak spots in the MHC class I loading and presentation route including loss of beta-2-microglobulin, TAP1/TAP2 mutations, LMP mutations, loss of heterozygocity in the MHC genes, and down regulation of specific MHC alleles.

Current cancer immunotherapy strategies typically employ the two arms of the immune system: the humoral and the cellular systems. In the first, systemic injection of high affinity monoclonal antibodies (mAbs) directed against cell surface tumor associated antigens has demonstrated statistically significant anti-tumor activity in clinical trials (5,6). Furthermore, anti-tumor mAbs that carry effectors such as cytokines or toxins are currently being evaluated in clinical trials (7). The second major approach for specific cancer immunotherapy employs the cellular arm of the immune system, mainly the CD8+ cytotoxic T-lymphocytes. Two major strategies are currently being used to increase the anti-tumor effectiveness of the cellular arm of the immune system: (i) active immunization of patients with peptides known to be recognized by T-lymphocytes, and (ii) adoptive transfer therapies that enable the selection, activation, and expansion of highly reactive T-cell subpopulations with improved anti-tumor potency. In the first approach, MHC-restricted peptides derived from recently identified tumor associated antigens (such as gp100, the MAGE group, NY-ESO-1) are used to vaccinate patients. These tumor specific antigen-derived peptides are highly specific due to their exclusive expression in specific tissues (8-11). The second strategy, adoptive cell transfer, has recently shown impressive results in metastatic melanoma patients in which highly selected, tumor-reactive T-cells against different over-expressed self-derived differentiation antigens were isolated, expended ex-vivo and reintroduced to the patients. In this approach, a persistent clonal repopulation of T-cells, proliferation in vivo, functional activity, and trafficking to tumor sites were demonstrated (12-14).

A new immunotherapeutic approach recently presented takes advantage of two well-established areas: (i) the known effectiveness of CD8+ cytotoxic T-lymphocytes in the elimination of cells presenting highly immunogenic MHC/peptide complexes, and (ii) the tumor-specific cell surface antigens targeting via recombinant fragments of antibodies, mainly single chain Fv fragments (scFvs). This approach utilizes a recombinant fusion protein composed of two functionally distinct entities: (i) a single-chain MHC class I molecule that carries a highly immunogenic tumor or viral-derived peptide, and (ii) a tumor-specific, high-affinity scFv fragment (15). Several groups have previously shown that a biotinylated MHC peptide multimerized on streptavidin or monomeric HLA-A2/influenza (Flu) matrix peptide complexes coupled via chemical conjugation to tumor-specific antibodies could induce in vitro T-lymphocyte-mediated lysis of coated tumor cells (16-20). However, these approaches utilize chemical conjugation and use whole antibodies or larger fragments, e.g. Fab fragments. However, production and homogeneity owing to the coupling strategy as well as tumor penetration capability are limited due to the large size of such molecules. Lev et al. describe a genetic fusion created between a single-chain recombinant HLA-A2 and tumor specific scFvs. These fusions were shown to be functional in vitro and in vivo, being able to specifically induce T-lymphocyte mediated in vitro and in vivo lysis of target-coated tumor cells (15). The stability of the new chimeric molecule is highly dependent on the presence of the peptide in the MHC groove. Therefore, dissociation of the peptide from the scHLA-A2 domain of the chimeric molecule can impair its stability. Oved et al. addressed this problem by constructing new chimeric molecules in which the peptide is connected to the scHLA-A2/scFv construct via a short linker. This new fusion protein was tested for its in vitro biochemical and biological activity (21).

There is a widely recognized need for a new fusion protein that can maintain its dual activity: bind tumor target cells through the scFv moiety as well as mediate potent, effective and specific cytotoxicity through the recruitment of CD8+ T-cells whose specificity is governed by the covalently linked HLA-A2-restricted peptide.

The MHC class I-restricted CD8+ cytotoxic T-cell (CTL) effector arm of the adaptive immune response is best equipped to recognize tumor cells as foreign and initiate the cascade of events resulting in tumor destruction. However, tumors have developed sophisticated strategies to escape immune effector mechanisms, of which the best-studied is the downregulation of MHC class I molecules which present the antigens recognized by CTLs.

To overcome the limitation of previous approaches and develop new approaches for immunotherapy, a recombinant molecule was constructed in which a single-chain MHC is specifically targeted to tumor cells through its fusion to cancer specific-recombinant antibody fragments or a ligand that binds to receptors expressed by tumor cells.

SUMMARY OF THE INVENTION

This invention provides a fusion protein comprising consecutive amino acids which, beginning at the amino terminus of the protein, correspond to consecutive amino acids present in (i) a cytomegalovirus human MHC-restricted peptide, (ii) a first peptide linker, (iii) a human β-2 microglobulin, (iv) a second peptide linker, (v) a HLA-A2 chain of a human MHC class I molecule, (vi) a third peptide linker, (vii) a variable region from a heavy chain of a scFv fragment of an antibody, and (viii) a variable region from a light chain of such scFv fragment, wherein the consecutive amino acids which correspond to (vii) and (viii) are bound together directly by a peptide bond or by consecutive amino acids which correspond to a fourth peptide linker and the scFv fragment is derived from an antibody which specifically binds to mesothelin.

This invention also provides compositions comprising the fusion protein and a carrier.

This invention further provides a nucleic acid construct encoding a fusion protein comprising consecutive amino acids which, beginning at the amino terminus of the protein, correspond to consecutive amino acids present in (i) a cytomegalovirus human MHC-restricted peptide, (ii) a first peptide linker, (iii) a human β-2 microglobulin, (iv) a second peptide linker, (v) a HLA-A2 chain of a human MHC class I molecule, (vi) a third peptide linker, (vii) a variable region from a heavy chain of a scFv fragment of an antibody, and (viii) a variable region from a light chain of such scFv fragment, wherein the consecutive amino acids which correspond to (vii) and (viii) are bound together directly by a peptide bond or by consecutive amino acids which correspond to a fourth peptide linker and the scFv fragment is derived from an antibody which specifically binds to mesothelin.

This invention still further provides an isolated preparation of bacterially-expressed inclusion bodies comprising over 30 percent by weight of a fusion protein in accordance with the invention.

This invention also provides a process for producing a fusion protein comprising culturing a transformed cell comprising the fusion protein, so that the fusion protein is expressed, and recovering the fusion protein so expressed.

This invention further provides a method of selectively killing a tumor cell which comprises contacting the cell with the fusion protein of the invention in an amount effective to initiate a CTL-mediated immune response against the tumor cell so as to thereby kill the tumor cell.

Finally, this invention further provides a method of treating a tumor cell which expresses mesothelin on its surface, which comprises contacting the tumor cell with the fusion protein according to the invention in an amount effective to initiate a CTL-mediated immune response against the tumor cell so as to thereby treat the tumor cell.

As an exemplary molecule of the present invention, a single-chain MHC molecule composed of $\beta_2$ microglobulin fused to the α1, α2 and α3 domains of HLA-A2 via a short peptide linker (15 amino acids) was fused to the scFv SS1 which targets mesothelin. To construct a fusion protein with covalently linked peptide a 9 amino acids peptide derived from the CMV pp65 protein NLVPMVATV (SEQ ID NO:4) was fused to the N-terminus of the scHLA-A2/SS1 (scFv) fusion protein via a 20 amino acid linker GGGGSGGGGSGGGGSGGGGS (SEQ ID NO:6). The fusion protein was expressed in E. coli and functional molecules were produced by in vitro refolding in the presence of CMV/scHLA-A2/SS1 (scFv). Flow cytometry studies revealed the ability to decorate antigen-positive, HLA-A2-negative human tumor cells with HLA-A2-peptide complexes in a manner that was entirely dependent upon the specificity of the targeting antibody fragment. Most importantly, CMV/scHLA-A2/SS1 (scFv)-mediated coating of target tumor cells made them susceptible for efficient and specific HLA-A2-restricted, CMV peptide-specific CTL-mediated lysis. These results demonstrate that antibody-guided tumor antigen-specific targeting of MHC-peptide complexes on tumor cells can render them susceptible to, and potentiate, CTL killing. This novel approach now opens the way for the development of new immunotherapeutic strategies based on antibody targeting of natural cognate MHC ligands and CTL-based cytotoxic mechanisms.

In connection with the present invention, a novel strategy was developed to re-target class I MHC-peptide complexes on the surface of tumor cells in a way that is independent of the extent of class I MHC expression by the target tumor cells. To this end, in one embodiment of the present invention, a molecule with two arms was employed. One arm, the targeting moiety, comprises tumor-specific recombinant fragments of antibodies directed to tumor or differentiation antigens which have been used for many years to target radioisotopes, toxins or drugs to cancer cells. The second effector arm is a single-chain MHC molecule (scMHC) composed of human β2-microglobulin linked to the three extracellular domains of the HLA-A2 heavy chain (24, 25, WO 01/72768). By connecting genes encoding the two arms in a single recombinant gene and expressing the gene, the new molecule is expressed efficiently in E. coli and produced, for example, by in vitro refolding in the presence of HLA-A2-CMV peptides. This approach, as described herein, renders the target tumor cells susceptible to lysis by cytotoxic T-cells regardless of their MHC expression level and thus may be employed as a new approach to potentiate CTL-mediated anti-tumor immunity. This novel approach will lead to the development of a new class of recombinant therapeutic agents capable of selective killing and elimination of tumor cells utilizing natural cognate MHC ligands and CTL-based cytotoxic mechanisms.

BRIEF DESCRIPTION OF THE FIGURES

FIGS. 1A-B

Schematic representation of scHLA-A2/SS1 (scFv) and a pep(CMV)/scHLA-A2/SS1 (scFv) (Compound A).

FIG. 1A illustrates the C-Terminus of the scHLA-A2 fused to the N-terminus of SS1 (scFv) via a 4 amino acid linker. FIG. 1B illustrates that the CMV pp65 peptide, i.e. NLVPMVATV (SEQ ID NO:4) was fused to the N-terminus of the scHLA-A2/SS1 (scFv) via a 20 amino acid linker GGGGSGGGGSGGGGSGGGGS (SEQ ID NO:6).

FIG. 2

Nucleic acid sequence encoding Compound A (SEQ ID NO:1).

FIGS. 3A-B

Expression and purification of Compound A.

Figure 3:
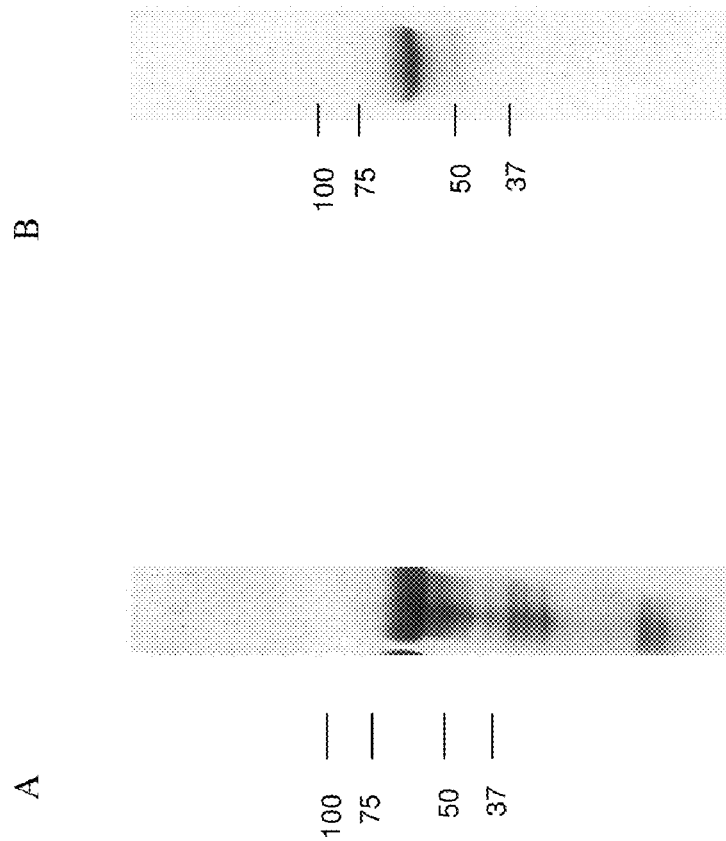

FIG. 3A shows the SDS/PAGE analysis of isolated inclusion bodies. FIG. 3B shows the SDS/PAGE analysis of Compound A after purification on ion-exchange chromatography.

FIG. 4

Binding of Compound A to recombinant mesothelin.

Mesothelin was immobilized on immuno-plates and dose-dependent binding of Compound A was monitored by conformation sensitive mAb W6 (33, 34).

FIGS. 5A-D

Binding of Compound A to mesothelin-expressing cells.

Figure 5:
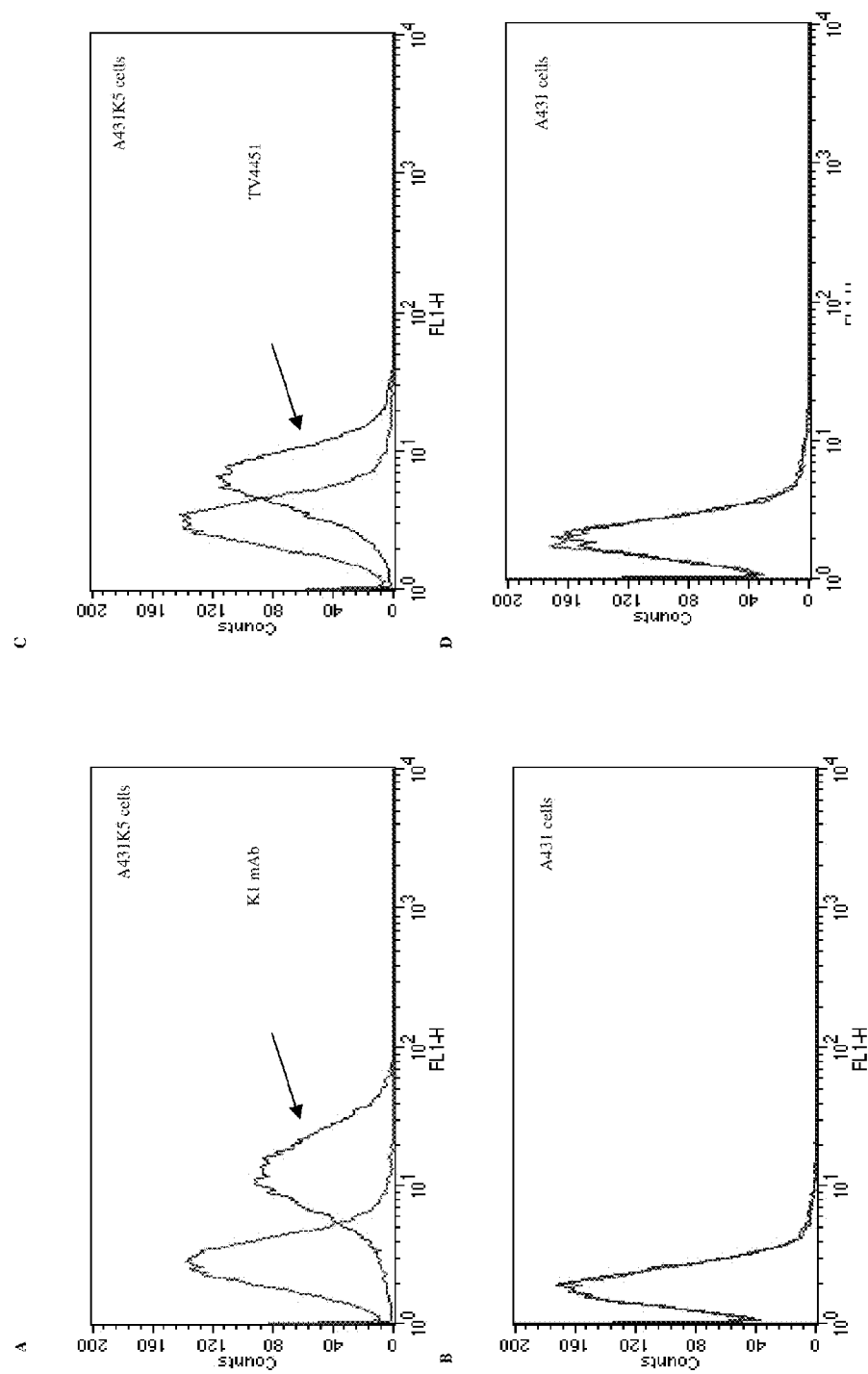

FIG. 5A-B demonstrates the flow cytometry analysis of the binding of Compound A to mesothelin-positive HLA-A2-negative A431K5 cells and mesothelin-negative HLA-A2-negative A431 cells. FIG. 5A shows the binding of the K1 mAb (31, 32) to A431K5 cells, and FIG. 5B shows the absence of binding of the K1 mAb to A431 cells. FIG. 5C shows the binding of Compound A to A431K5 cells, and FIG. 5D shows the absence of binding of Compound A to A431 cells. The binding was monitored using anti-HLA-A2 specific antibody BB7.2 (35) and a FITC-labeled secondary antibody.

FIGS. 6A-B

Figure 6:
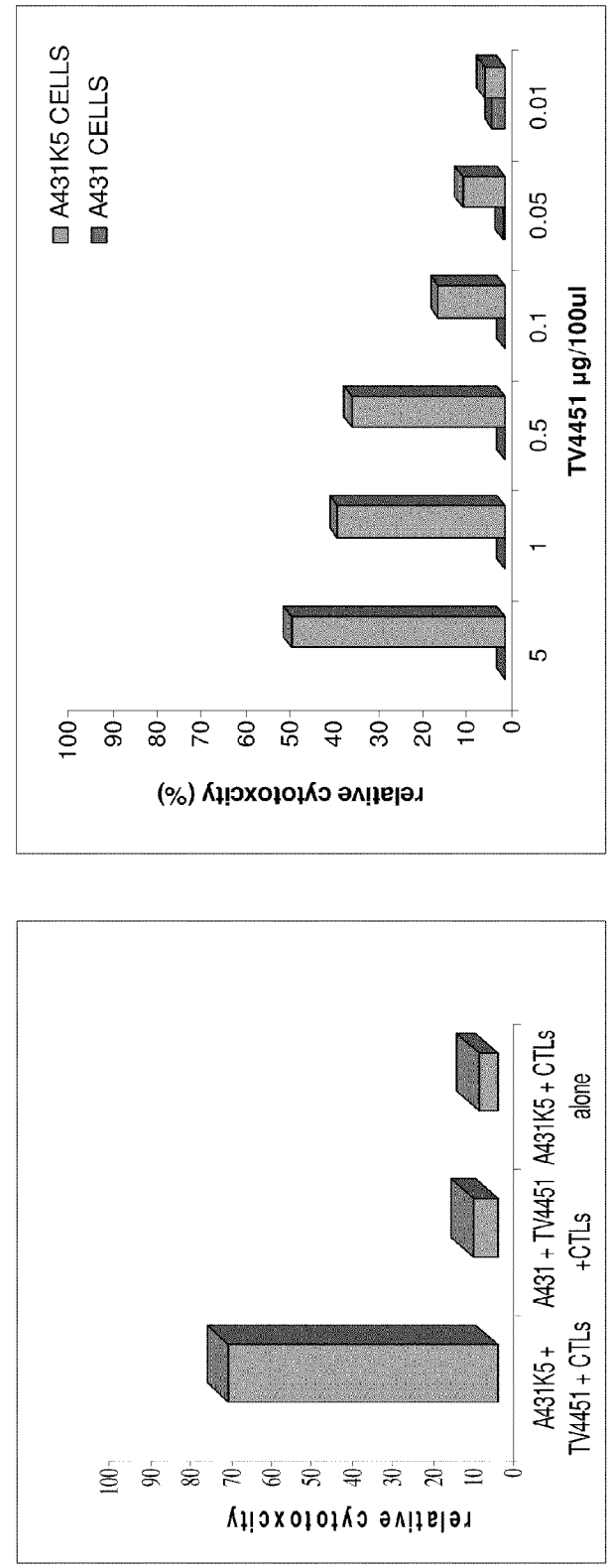
Figure 7:
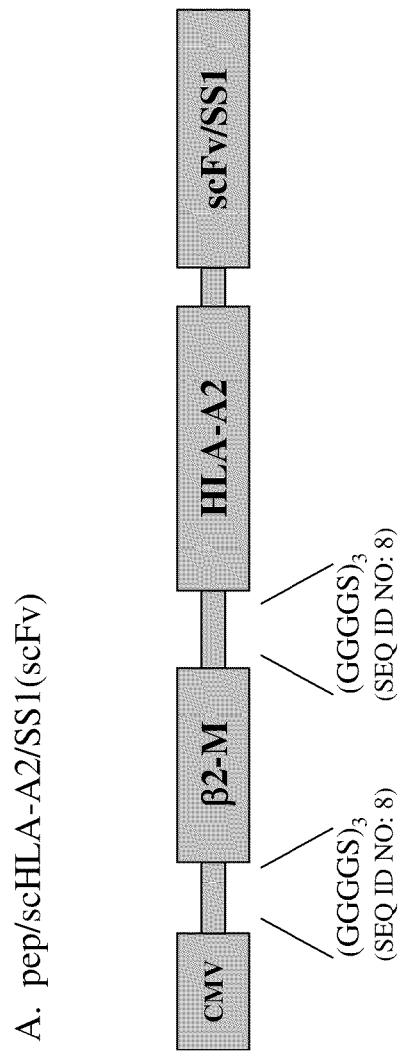

Potentiation of CTL-mediated lysis of HLA-A2 negative tumor cells by Compound A. In FIG. 6A, the mesothelin-transfected A431K5 cells and the parental mesothelin-negative A431 cells were incubated with Compound A (10 μg) and CMV specific CTLs in a [$S^{35}$] methionine release assay. FIG. 6B demonstrates dose-dependent activity of Compound A when mesothelin-transfected A431K5 cells and the parental mesothelin-negative A431 cells were incubated with different concentrations of Compound A and CMV-specific CTLs in a [$S^{35}$] methionine release assay.

FIG. 7

Schematic representation of the pep/scHLA-A2/SS1 (scFv) (Compound B). In Compound B, the peptide NLVP-MVATV (SEQ ID NO:4) was fused to the N-terminus of scHLA-A2/SS1 (scFv) via a 15 amino acid linker GGGGSGGGGSGGGGS (SEQ ID NO:8).

FIG. 8

Nucleic acid sequence encoding Compound B (SEQ ID NO:22).

FIGS. 9A-B

Expression and purification of Compound B.

Figure 9:
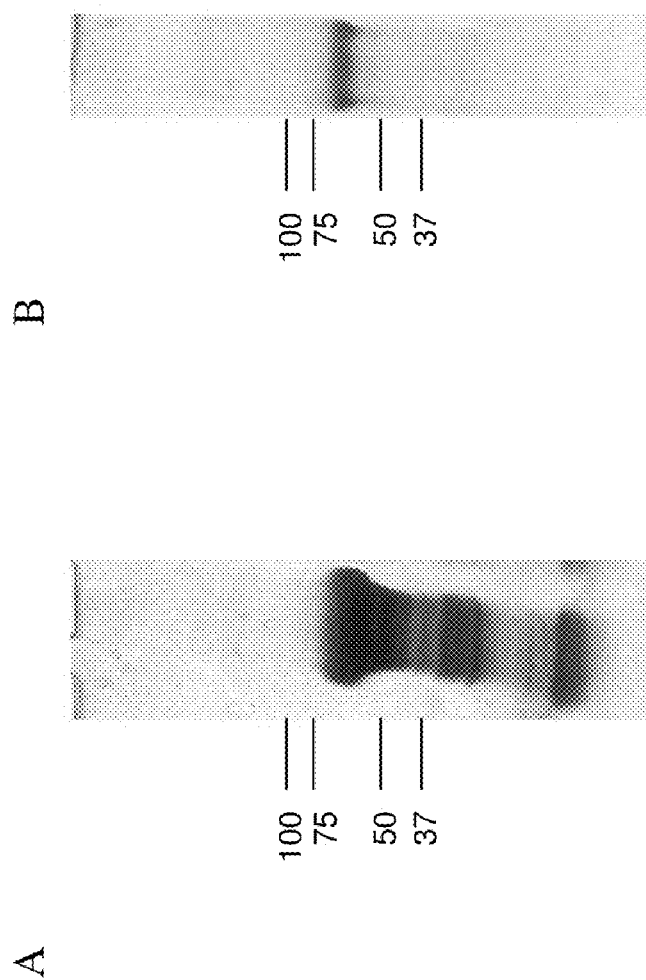

FIG. 9A shows SDS/PAGE analysis of isolated inclusion bodies. FIG. 9B shows SDS/PAGE analysis of Compound B after purification on ion-exchange chromatography.

FIGS. 10A-F

Binding of Compound B to mesothelin-expressing cells.

Figure 10:
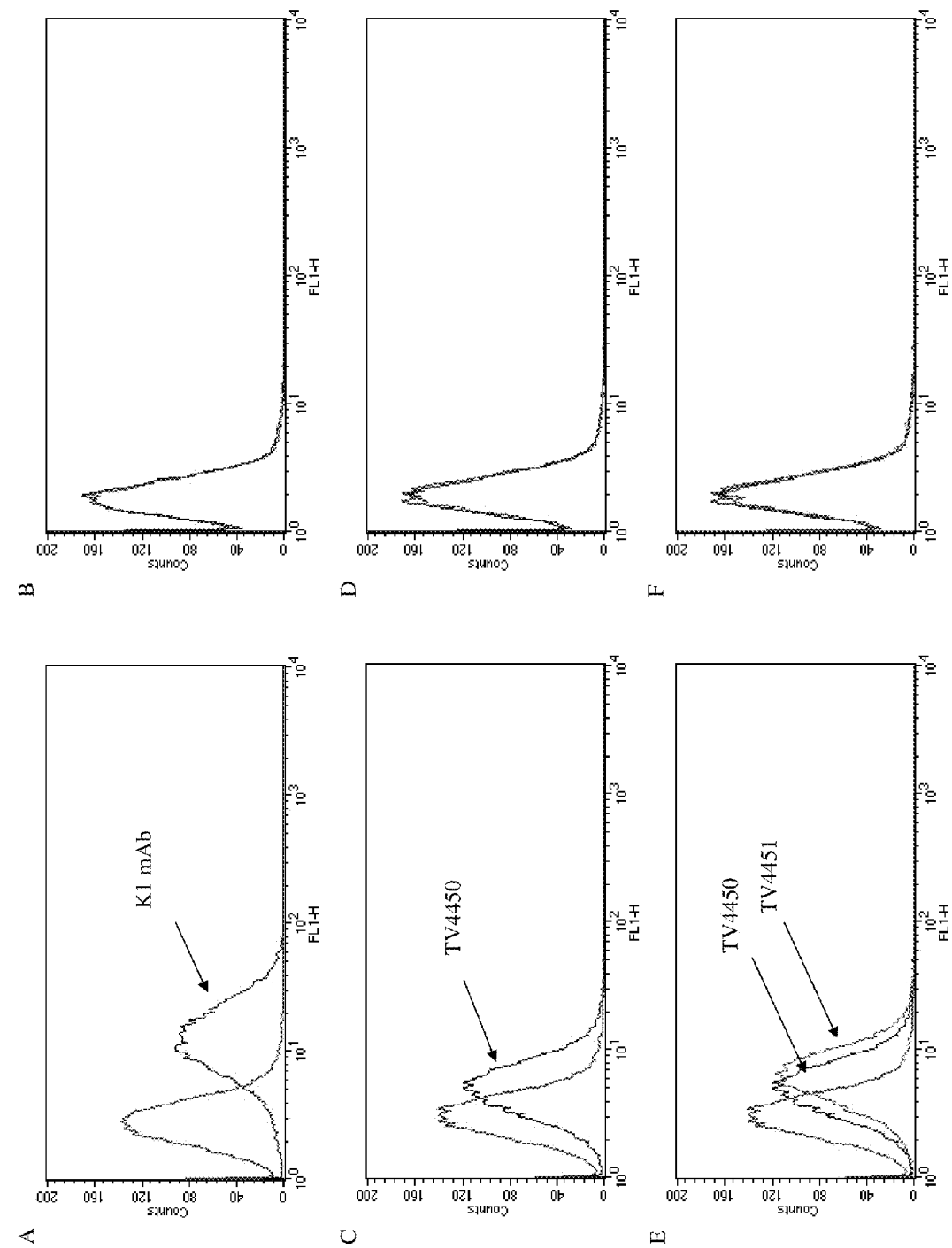

FIGS. 10A-F demonstrate the flow cytometry analysis of the binding of Compound B to mesothelin-positive HLA-A2-negative A431K5 cells and mesothelin-negative HLA-A2-negative A431 cells. FIG. 10A shows the binding of K1 mAb to A431K5 cells, and FIG. 10B shows the lack of binding of K1 mAb to A431 cells (B). FIG. 10C shows the binding of Compound B to A431K5 cells, and FIG. 10D shows the lack of binding of Compound B to A431 cells. FIG. 10E shows the comparison between the binding of Compound A and Compound B to A431K5 cells, and FIG. 10F shows the lack of binding of Compound A and Compound B to A431 cells. The binding was monitored using anti-HLA-A2 specific antibody BB7.2 and a FITC-labeled secondary antibody.

FIGS. 11A-B

Potentiation of CTL-mediated lysis of HLA-A2-negative tumor cells by Compound B.

Figure 11:
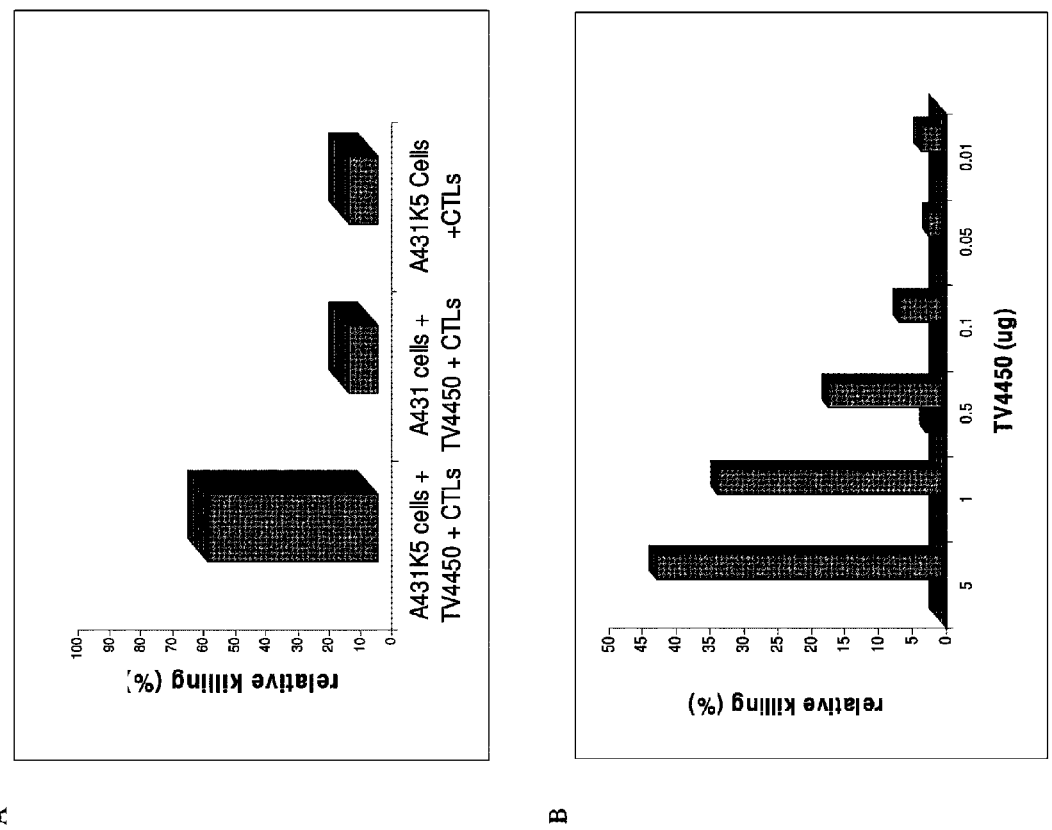

In FIG. 11A, mesothelin-transfected A431K5 cells and the parental mesothelin-negative A431 cells were incubated with Compound B (10 μg) and CMV-specific CTLs in a [$S^{35}$] methionine release assay. FIG. 11B demonstrates dose-dependent activity of Compound B, when mesothelin-transfected A431K5 cells and the parental mesothelin-negative A431 cells were incubated with different concentrations of Compound A and CMV-specific CTLs in a [$S^{35}$] methionine release assay

FIG. 12

Potentiation of CTL-mediated lysis of HLA-A2 negative tumor cells by Compound B and Compound A. Mesothelin-transfected A431K5 cells and the parental mesothelin-negative A431 cells were incubated with different concentrations of Compound B or Compound A and with CMV-specific CTLs in a [$S^{35}$] methionine release assay. The figure shows results of incubation of Compound A with A431K5 cells, incubation of Compound B with A431K5 cells, incubation of Compound A with A431 cells, and incubation of Compound B with A431 cells.

FIGS. 13A-B

Schematic representation of scHLA-A2/SS1 (scFv) and M1cov/scHLA-A2/SS1 (scFv).

FIG. 13A shows the C-terminus of the scHLA-A2 fused to the N-terminus of scFv via 4 amino acid linker. FIG. 13B shows the M158-66 peptide fused to the N-terminus of the scHLA-A2/SS1 (scFv) via a 15 amino acid linker GGGGSGGGGSGGGGS (SEQ ID NO:8).

FIG. 14

Nucleic acid sequence encoding the M1cov/scHLA-A2/SS1 (scFv) fusion protein (SEQ ID NO:23).

FIGS. 15A-B

Expression and purification of the M1-cov/scHLA-A2/SS1 (scFv) fusion protein.

Figure 15:
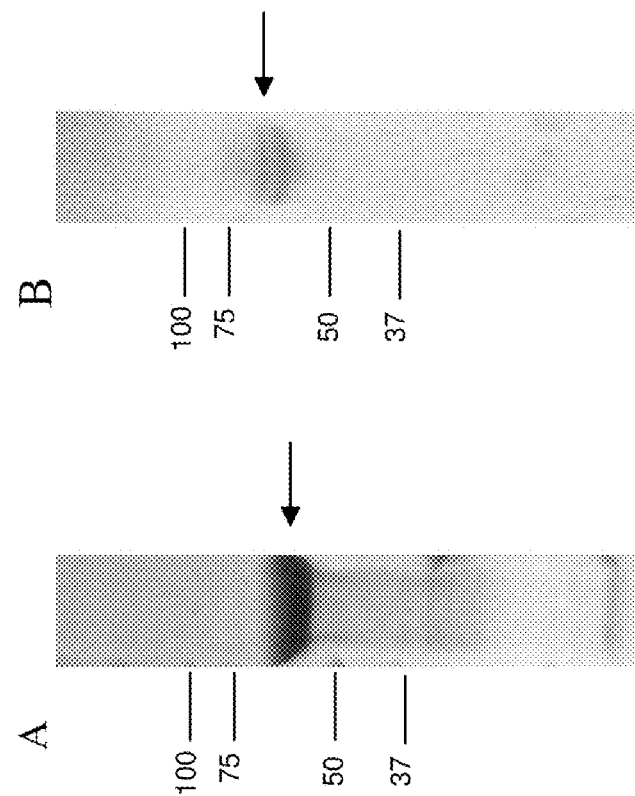

FIG. 15A shows the SDS/PAGE analysis of isolated inclusion bodies. FIG. 15B shows the SDS/PAGE analysis of M1-cov/scHLA-A2/SS1 (scFv) fusion protein after purification on ion-exchange chromatography.

FIG. 16

Binding of the M1-cov/scHLA-A2/SS1 (scFv) fusion protein to recombinant Mesothelin. Mesothelin was immobilized onto immuno-plates and dose-dependent binding of M1-cov/scHLA-A2/SS1 (scFv) was monitored by conformation sensitive mAb (W6).

FIGS. 17A-D

Figure 17:
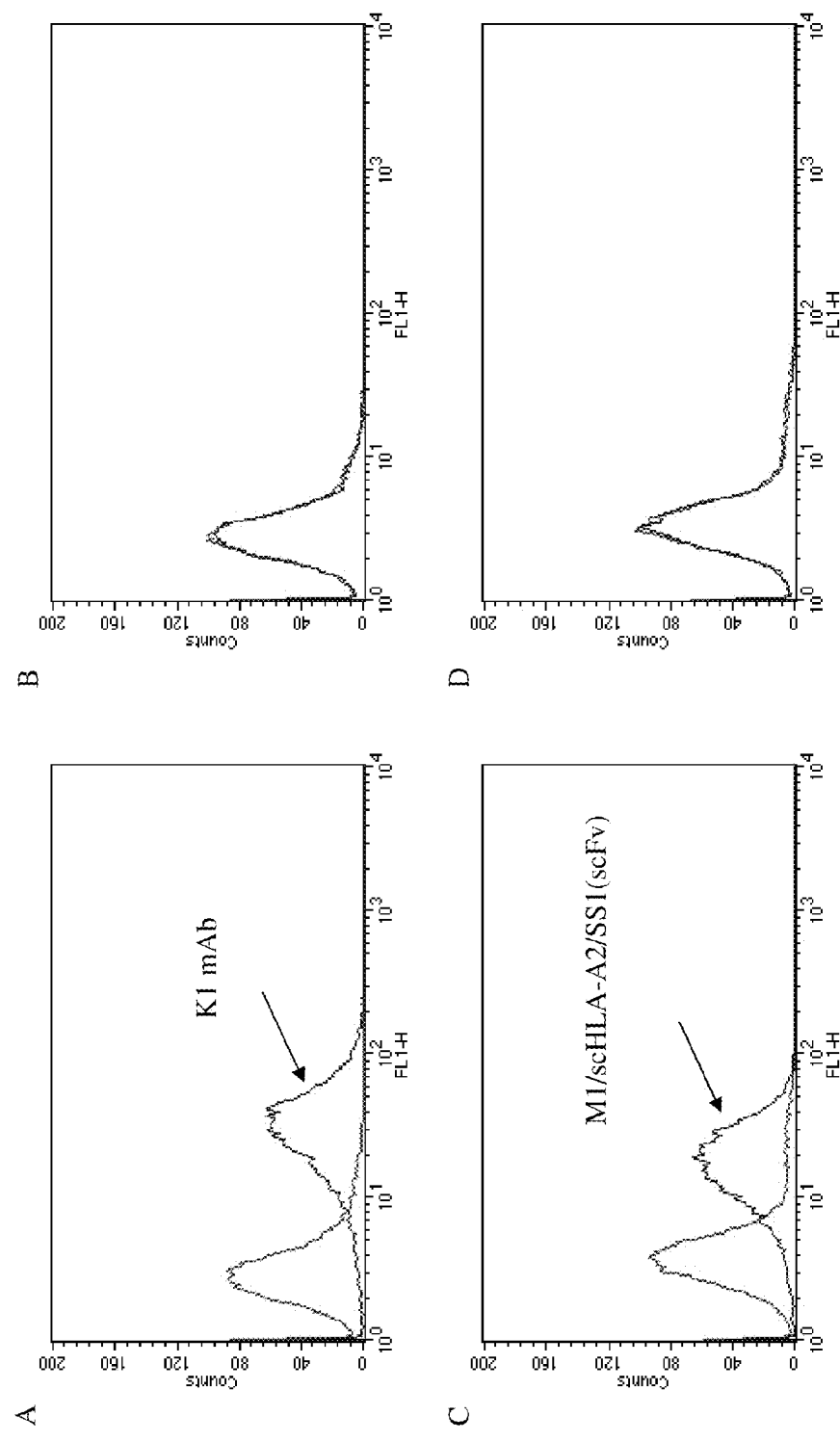
Figure 18:
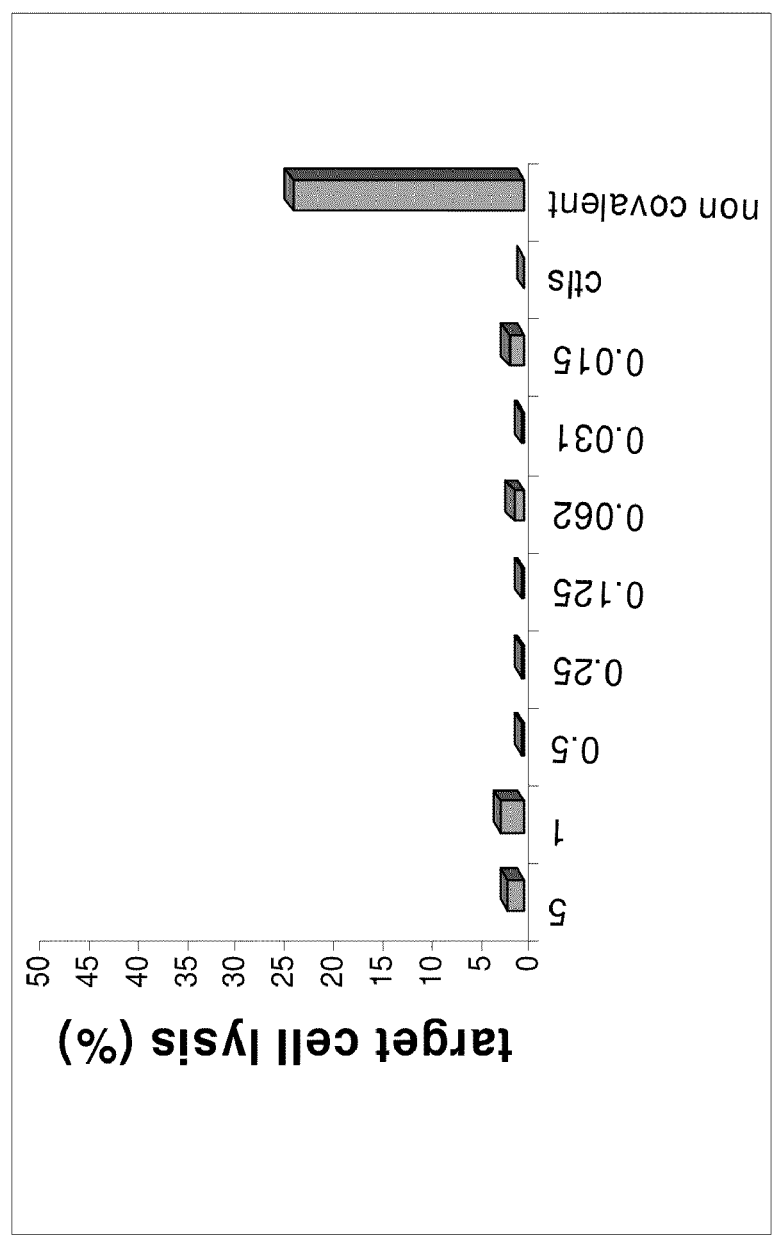

Binding of M1-cov/scHLA-A2/SS1 (scFv) fusion protein to Mesothelin expressing cells. FIGS. 17A-D show flow cytometry analysis of the binding of M1-cov/scHLA-A2/SS1 (scFv) to mesothelin-positive HLA-A2-negative A431K5 cells and mesothelin-negative HLA-A2-negative A431 cells. FIG. 17A shows the binding of K1 mAb to A431K5 cells, and FIG. 17B shows the absence of binding of K1 mAb to A431 cells. FIG. 17C shows the binding of M1-cov/scHLA-A2/SS1 (scFv) fusion protein to A431K5 cells, and FIG. 17D shows the absence of binding of M1-cov/scHLA-A2/SS1 (scFv) fusion protein to A431 cells. The binding was monitored using anti-HLA-A2 specific antibody BB7.2 and a FITC-labeled secondary antibody.

FIG. 18

Potentiation of CTL-mediated lysis of HLA-A2-negative tumor cells by M1-cov/scHLA-A2/SS1 (scFv) fusion protein. Mesothelin-transfected A431K5 cells and the parental mesothelin-negative A431 cells were incubated with different concentration of M1-cov/scHLA-A2/SS1 (scFv) and with M1 specific HLA-A2-restricted CTLs in a [$S^{35}$]methionine release assay.

DETAILED DESCRIPTION OF THE INVENTION

This invention provides a fusion protein comprising consecutive amino acids which, beginning at the amino terminus of the protein, correspond to consecutive amino acids present in (i) a cytomegalovirus human MHC-restricted peptide, (ii) a first peptide linker, (iii) a human β-2 microglobulin, (iv) a second peptide linker, (v) a HLA-A2 chain of a human MHC class I molecule, (vi) a third peptide linker, (vii) a variable region from a heavy chain of a scFv fragment of an antibody, and (viii) a variable region from a light chain of such scFv fragment, wherein the consecutive amino acids which correspond to (vii) and (viii) are bound together directly by a peptide bond or by consecutive amino acids which correspond to a fourth peptide linker and the scFv fragment is derived from an antibody which specifically binds to mesothelin. In one embodiment, the first peptide linker has the amino acid sequence GGGGSGGGGSGGGGSGGGGS (SEQ ID NO:6). In another embodiment, the second peptide linker has the amino acid sequence GGGGSGGGGSGGGGS (SEQ ID NO:8). In another embodiment, the third peptide linker has the amino acid sequence ASGG (SEQ ID NO:10). In another embodiment, the fourth peptide linker has the amino acid sequence GVGGSGGGGSGGGGS (SEQ ID NO:19). In another embodiment, the cytomegalovirus human MHC-restricted peptide has the amino acid sequence NLVP-MVATV (SEQ ID NO:4).

As used herein, "first peptide linker", "second peptide linker" and "fourth peptide linker" refer to peptides composed of a monomeric peptide whose amino acid sequence is GXGGS (SEQ ID NO:20) or a multimer thereof, wherein X may be any amino acid. These peptide linkers may be a multimer of 2-10 of such monomeric peptide. In any such multimer, each monomeric peptide may be the same as or different from other monomeric peptide in the multimer depending on the identity of amino acid X. In one embodiment, X in the monomeric peptide is the amino acid valine (V). In another embodiment, X in the monomeric peptide is the amino acid glycine (G). In presently preferred embodiments, the peptide linker comprises a multimer of three or four monomeric peptides, particularly a multimer of three monomeric peptides in which the most N-terminal X is the amino acid V, and the second and third X are the amino acid G.

In one embodiment, the sequence of the consecutive amino acids corresponding to (vii), followed by the fourth peptide linker, followed by (viii) is set forth in SEQ ID NO:12.

In another embodiment, the consecutive amino acids of the fusion protein, Compound A, have the amino acid sequence set forth in SEQ ID NO:2.

This invention also provides a composition comprising a fusion protein in accordance with the invention and a carrier. In one embodiment, the fusion protein is present in the composition in a therapeutically effective amount and the carrier is a pharmaceutically acceptable carrier.

This invention also provides a nucleic acid construct encoding a fusion protein comprising consecutive amino acids which, beginning at the amino terminus of the protein, correspond to consecutive amino acids present in (i) a cytomegalovirus human MHC-restricted peptide, (ii) a first peptide linker, (iii) a human β-2 microglobulin, (iv) a second peptide linker, (v) a HLA-A2 chain of a human MHC class I molecule, (vi) a third peptide linker, (vii) a variable region from a heavy chain of a scFv fragment of an antibody, and (viii) a variable region from a light chain of such scFv fragment, wherein the consecutive amino acids which correspond to (vii) and (viii) are bound together directly by a peptide bond or by consecutive amino acids which correspond to a fourth peptide linker and the scFv fragment is derived from an antibody which specifically binds to mesothelin. In one embodiment, the nucleic acid construct has the nucleic acid sequence set forth in SEQ ID NO:1.

This invention also provides a vector comprising the nucleic acid construct of the invention. Examples of such vectors are plasmids, viruses, phages, and the like.

This invention further provides an expression vector comprising the nucleic acid construct of the invention and a promoter operatively linked thereto.

This invention also provides a transformed cell comprising a vector according to the invention. The transformed cell may be a eukaryotic cell, e.g. one selected from the group consisting of a mammalian cell, an insect cell, a plant cell, a yeast cell and a protozoa cell. Alternatively, the transformed cell may be a bacterial cell.

This invention provides an isolated preparation of bacterially-expressed inclusion bodies comprising over 30 percent by weight of a fusion protein according to the invention.

This invention also provides a process for producing a fusion protein comprising culturing the transformed cell of the invention so that the fusion protein is expressed, and recovering the fusion protein so expressed. In one embodiment, the recovery of the fusion protein comprises subjecting the expressed fusion protein to size exclusion chromatography. In another embodiment, the fusion protein is expressed in inclusion bodies. In one embodiment, the process further comprises treating the inclusion bodies so as to separate and refold the fusion protein and thereby produce the fusion protein in active form. In another embodiment, treating of the inclusion bodies to separate the fusion protein therefrom comprises contacting the inclusion bodies with a denaturing agent.

As used herein, an "active form" of the fusion protein means a three dimensional conformation of the fusion protein which permits the fusion protein to specifically bind to mesothelin when mesothelin is present on the surface of a tumor cell.

This invention also provides a method of selectively killing a tumor cell, which comprises contacting the cell with the fusion protein of the invention in an amount effective to initiate a CTL-mediated immune response against the tumor cell so as to thereby kill the tumor cell. In one embodiment, the tumor cell is in a patient and the contacting is effected by administering the fusion protein to the patient.

This invention further provides a method of treating a tumor cell which expresses mesothelin on its surface, which comprises contacting the tumor cell with the fusion protein according to the invention in an amount effective to initiate a CTL-mediated immune response against the tumor cell so as to thereby treat the tumor cell. In one embodiment, the tumor cell is present in a solid tumor. In another embodiment, the solid tumor is a tumor associated with ovarian, lung, pancreatic or head/neck cancer, or mesothelioma.

The present invention provides (i) novel fusion proteins; (ii) processes of preparing same; (iii) nucleic acid constructs encoding same; and (iv) methods of using same for selective killing of cells, cancer cells in particular.

The principles and operation of the present invention may be better understood with reference to the figures and description set forth herein.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

Tumor progression is often associated with the secretion of immune-suppressive factors and/or the down-regulation of MHC class I antigen-presentation functions (2). Even when a specific CTL response is demonstrated in patients, this response is low because the anti-tumor CTL population is rare, very infrequent, and in some cases the CLTs are not functional or anergic (26). Moreover, it is well-established that the number of MHC-peptide complexes on the surface of tumor cells that present a particular tumor-associated peptide is low (27). Significant progress toward developing vaccines that can stimulate an immune response against tumors has involved the identification of the protein antigens associated with a given tumor type and epitope mapping of tumor antigens for MHC class I and class II restricted binding motifs were identified and are currently being used in various vaccination programs (14, 11, 8). MHC class I molecules presenting the appropriate peptides are necessary to provide the specific signals for recognition and killing by CTLs. However, the principal mechanism of tumor escape is the loss, downregulation or alteration of HLA profiles that may render the target cell unresponsive to CTL lysis, even if the cell expresses the appropriate tumor antigen.

The present invention provides a new approach to circumvent this problem. While reducing the present invention to practice, tumor-specific targeting of class I MHC-peptide complexes on tumor cells was shown to be an effective and efficient strategy to render HLA-A2-negative cells susceptible to lysis by relevant HLA-A2-restricted CTLs. This new strategy of redirecting CTLs against tumor cells takes advantage of the use of recombinant anti-mesothelin antibody fragment and CMV ligand that can localize on malignant cells that express a tumor with a relatively high degree of specificity.

The anti-mesothelin antibody targeting fragment and CMV ligand are fused to a single-chain HLA-A2 molecule that can be folded efficiently and functionally.

The results presented herein provide a clear demonstration of the usefulness of the approach of the present invention to recruit active CTLs for tumor cell killing via cancer-specific antibody or ligand guided targeting of scMHC-peptide complexes. These results pave the way for the development of a new immunotherapeutic approach based on naturally occurring cellular immune responses which are redirected against the tumor cells.

It will be appreciated that the fusion protein of the present invention or portions thereof can be prepared by several ways, including solid phase protein synthesis. However, in the preferred embodiment of the invention, at least major portions of the molecules, e.g., the scHLA-A2 domain (with or without the CMV peptide) and the scFV domain are generated by translation of a respective nucleic acid construct or constructs encoding the molecule.

Accordingly, one to three open reading frames are required to synthesize the molecules of FIG. 1B via translation. These open reading frames can reside on a single, two or three nucleic acid molecules. Thus, for example, a single nucleic acid construct can carry one, two or all three open reading frames. One to three cis-acting regulatory sequences can be used to control the expression of the one to three open reading frames. For example, a single cis-acting regulatory sequence can control the expression of one, two or three open reading frames, in a cistrone-like manner. In the alternative, three independent cis-acting regulatory sequences can be used to control the expression of the three open reading frames. Other combinations are also envisaged.

The open reading frames and the cis-acting regulatory sequences can be carried by one to three nucleic acid molecules. For example, each open reading frame and its cis-acting regulatory sequence is carried by a different nucleic acid molecule, or all of the open reading frames and their associated cis-acting regulatory sequences are carried by a single nucleic acid molecule. Other combinations are also envisaged.

Expression of the fusion protein can be effected by transformation/transfection and/or co-transformation/co-transfection of a single cell or a plurality of cells with any of the nucleic acid molecules, serving as transformation/transfection vectors (e.g., as plasmids, phages, phagemids or viruses).

It will be appreciated that the fusion protein whose amino acid sequence is set forth in SEQ ID NO:2 and includes the N-terminal amino acid methionine, likely represents the fusion protein as expressed in a bacterial cell. Depending on the specific bacterial cell employed to express the fusion protein, the N-terminal methionine may be cleaved and removed. Accordingly, it is contemplated that fusion proteins in accordance with this invention encompass both those with, and those without, a N-terminal methionine. In general, when a fusion protein in accordance with the invention is expressed in a eukaryotic cell, it would lack the N-terminal methionine. Therefore, it is to be appreciated that the amino acid sequence of expressed fusion proteins according to the invention may include or not include such N-terminal methionine depending on the type of cells in which the proteins are expressed.

Whenever and wherever used, the linker peptide is selected of an amino acid sequence which is inherently flexible, such that the polypeptides connected thereby independently and natively fold following expression thereof, thus facilitating the formation of a functional or active single chain (sc) human $\beta_2$M/HLA complex, antibody targeting or human $\beta_2$M/HLA-CMV restricted antigen complex.

Any of the nucleic acid constructs described herein comprise at least one cis-acting regulatory sequence operably linked to the coding polynucleotides therein. Preferably, the cis-acting regulatory sequence is functional in bacteria. Alternatively, the cis-acting regulatory sequence is functional in yeast. Still alternatively, the cis-acting regulatory sequence is functional in animal cells. Yet alternatively, the cis acting regulatory sequence is functional in plant cells.

The cis-acting regulatory sequence can include a promoter sequence and additional transcriptional or a translational enhancer sequences all of which serve for facilitating the expression of the polynucleotides when introduced into a host cell. Specific examples of promoters are described hereinbelow in context of various eukaryotic and prokaryotic expression systems and in the examples section which follows.

It will be appreciated that a single cis-acting regulatory sequence can be utilized in a nucleic acid construct to direct transcription of a single transcript which includes one or more open reading frames. In the later case, an internal ribosome entry site (IRES) can be utilized so as to allow translation of the internally positioned nucleic acid sequence.

Whenever co-expression of independent polypeptides in a single cell is of choice, the construct or constructs employed must be configured such that the levels of expression of the independent polypeptides are optimized, so as to obtain highest proportions of the final product.

Preferably a promoter (being an example of a cis-acting regulatory sequence) utilized by the nucleic acid construct(s) of the present invention is a strong constitutive promoter such that high levels of expression are attained for the polynucleotides following host cell transformation.

It will be appreciated that high levels of expression can also be effected by transforming the host cell with a high copy number of the nucleic acid construct(s), or by utilizing cis acting sequences which stabilize the resultant transcript and as such decrease the degradation or "turn-over" of such a transcript.

As used herein, the phrase "transformed cell" describes a cell into which an exogenous nucleic acid sequence is introduced to thereby stably or transiently genetically alter the host cell. It may occur under natural or artificial conditions using various methods well known in the art some of which are described in detail hereinbelow in context with specific examples of host cells.

The transformed host cell can be a eukaryotic cell, such as, for example, a mammalian cell, an insect cell, a plant cell, a yeast cell and a protozoa cell, or alternatively, the cell can be a bacterial cell.

When utilized for eukaryotic host cell expression, the nucleic acid construct(s) according to the present invention can be a shuttle vector, which can propagate both in *E. coli* (wherein the construct comprises an appropriate selectable marker and origin of replication) and be compatible for expression in eukaryotic host cells. The nucleic acid construct(s) according to the present invention can be, for example, a plasmid, a bacmid, a phagemid, a cosmid, a phage, a virus or an artificial chromosome.

Suitable mammalian expression systems include, but are not limited to, pcDNA3, pcDNA3.1(±), pZeoSV2(±), pSecTag2, pDisplay, pEF/myc/cyto, pCMV/myc/cyto, pCR3.1, which are available from Invitrogen™ Corporation (Carlsbad, Calif. USA), pCI which is available from Promega™ Corporation (Madison Wis. USA), pBK-RSV and PBK-CMV which are available from Stratagene® (La Jolla, Calif. USA), pTRES which is available from Clontech® Laboratories, Inc. (Mountain View, Calif. USA), and their derivatives.

Insect cell cultures can also be utilized to express the nucleic acid sequences of the present invention. Suitable insect expression systems include, but are not limited to the baculovirus expression system and its derivatives which are commercially available from numerous suppliers such as maxBac™ (Invitrogen™ Corporation, Carlsbad, Calif. USA) BacPak™ (Clontech® Laboratories, Inc. Mountain View, Calif. USA), or Bac-to-Bac™ (Invitrogen™/Gibco®, Carlsbad, Calif. USA).

Expression of the nucleic acid sequences of the present invention can also be effected in plants cells. As used herein, the phrase "plant cell" can refer to plant protoplasts, cells of a plant tissue culture, cells of plant derived tissues or cells of whole plants.

There are various methods of introducing nucleic acid constructs into plant cells. Such methods rely on either stable integration of the nucleic acid construct or a portion thereof into the genome of the plant cell, or on transient expression of the nucleic acid construct in which case these sequences are not stably integrated into the genome of the plant cell.

There are two principle methods of effecting stable genomic integration of exogenous nucleic acid sequences such as those included within the nucleic acid construct of the present invention into plant cell genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil; L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure, see for example, Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of stably transformed dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues. Direct DNA transfer can also be utilized to transiently transform plant cells.

In any case suitable plant promoters which can be utilized for plant cell expression of the first and second nucleic acid sequences, include, but are not limited to CaMV 35S promoter, ubiquitin promoter, and other strong promoters which can express the nucleic acid sequences in a constitutive or tissue specific manner.

Plant viruses can also be used as transformation vectors. Viruses that have been shown to be useful for the transformation of plant cell hosts include CaV, TMV and BV. Transformation of plants using plant viruses is described in U.S. Pat. No. 4,855,237 (BGV), EPA 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the nucleic acid sequences described above. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

Yeast cells can also be utilized as host cells by the present invention. Numerous examples of yeast expression vectors suitable for expression of the nucleic acid sequences of the present invention in yeast are known in the art and are commercially available. Such vectors are usually introduced in a yeast host cell via chemical or electroporation transformation methods well known in the art. Commercially available systems include, for example, the pYES™ (Invitrogen™ Corporation, Carlsbad Calif., USA) or the YEX™ (Clontech® Laboratories, Mountain View, Calif. USA) expression systems.

It will be appreciated that when expressed in eukaryotic expression systems such as those described above, the nucleic acid construct preferably includes a signal peptide encoding sequence such that the polypeptides produced from the first and second nucleic acid sequences are directed via the attached signal peptide into secretion pathways. For example, in mammalian, insect and yeast host cells, the expressed polypeptides can be secreted to the growth medium, while in plant expression systems the polypeptides can be secreted into the apoplast, or directed into a subcellular organelle.

A bacterial host can be transformed with the nucleic acid sequence via transformation methods well known in the art, including for example, chemical transformation (e.g., $CaCl_2$) or electroporation.

Numerous examples of bacterial expression systems which can be utilized to express the nucleic acid sequences of the present invention are known in the art. Commercially available bacterial expression systems include, but are not limited to, the pET™ expression system (Novagen®, EMB Biosciences, San Diego, Calif. USA), pSE™ expression system (Invitrogen™ Corporation, Carlsbad Calif., USA) or the pGEX™ expression system (Amersham Biosciences, Piscataway, N.J. USA).

As is further described in the Experimental Details section which follows, bacterial expression is particularly advantageous since the expressed polypeptides form substantially pure inclusion bodies readily amenable to recovery and purification of the expressed polypeptide.

Thus, this invention provides a preparation of bacterial-expressed inclusion bodies which are composed of over 30%, preferably over 50%, more preferably over 75%, most preferably over 90% by weight of the fusion protein or a mixture of fusion proteins of the present invention. The isolation of such inclusion bodies and the purification of the fusion protein(s) therefrom are described in detail in the Experimental Details section which follows. Bacterial expression of the fusion protein(s) can provide high quantities of pure and active forms of fusion proteins.

As is further described in the Experimental Details section which follows, the expressed fusion proteins form substantially pure inclusion bodies which are readily isolated via fractionation techniques well known in the art and purified via for example denaturing-renaturing steps.

The fusion proteins of the invention may be renatured and refolded in the presence of a MHC-restricted peptide, which is either linked to, co-expressed with or mixed with other polypeptides of the invention and being capable of binding the single chain MHC class I polypeptide. As is further described in the examples section, this enables to generate a substantially pure MHC class I-antigenic peptide complex which can further be purified via size exclusion chromatography.

It will be appreciated that the CMV peptide used for refolding can be co-expressed along with (as an independent peptide) or be fused to the scHLA-A2 chain of the MHC Class I molecule in the bacteria. In such a case the expressed fusion protein and peptide co-form inclusion bodies which can be isolated and utilized for MHC class I-antigenic peptide complex formation.

The following section provides specific examples for each of the various aspects of the invention described herein. These examples should not be regarded as limiting in any way, as the invention can be practiced in similar, yet somewhat different ways. These examples, however, teach one of ordinary skills in the art how to practice various alternatives and embodiments of the invention.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Details

Materials and Methods:

Cloning of Compound A

The scHLA-A2/SS1 (scFv) was constructed as previously described by linking the C-terminus of scHLA-A2 to the N-terminus of the SS1 scFv via a short linker ASGG (SEQ ID NO:4) (15). To construct the scHLA-A2/SS1 (scFv) with covalently bound MHC-restricted peptide, the MHC-restricted peptide was fused with the peptide linker GGGGSGGGGSGGGGSGGGGS (SEQ ID NO:6) to the N-terminus of the scHLA-A2/SS1 (scFv) molecule by a PCR overlap extension reaction with the primers: 5'M1-5'GGAAGCGTTGGCGCATATGGGCAT-TCTGGGCTTCGTGTTTACC CTGGGCGGAGGAG-GATCCGGTGGCGGAGGTTCAGGAGGCGGTGGAT-CGA TCCAGCGTACTCCAAAG3'(SEQ ID NO: 13) and 3'VLscSS1-5'GCAGTAAGGAATTCTCATTATTT-TATTTCCAACTTTGT3'(SEQ ID NO: 14) In the 5'M1 primer a silence mutation was inserted at the linker sequence, this change in sequence creates a BamH1 restriction site.

The PCR products were sub-cloned to TA cloning vector (pGEM-T Easy Vector, Promega™ Corporation, Madison, Wis. USA) and subsequently to a T7 promoter-based expression vector (PRB) using the NdeI and EcoRI restriction sites.

To generate Compound A, M1/scHLA-A2/SS1 (scFv) was used as a template for ligation with dsDNA primer. The M1/scHLA-A2/SS1 (scFv) (in PRB plasmid) was digested with NdeI and BamHI, and the plasmid fraction was ligated to dsDNA primer containing the CMV peptide sequence and the extension of the linker sequence 5'CMVcovLL (cassette): 5'TATGAACCTGGTGCCGATGGTCGCGACCGT TGGAGGTGGCGGTTCTGGCGGAGGAG-3' (SEQ ID NO: 15) and 3'CMVcovLL (cassette):5'GATC CTCCTC-CGCCAGAACCGCCACCTCCAACGGTCGC-GACCATCGGCACCAGG TTCA3'(SEQ ID NO:16). The annealing of the primers (5'CMVcovLL (cassette) and 3'CMVcovLL (cassette)) was performed by incubating the primers at 95° C. for 2 min followed by 1 h incubation at room temperature. The ligation product was transformed to E-coli DH5α for plasmid amplification. Plasmid was purified by QIAGEN® Miniprep™, DNA isolation kit (Qiagen®, Inc., Valencia, Calif. USA) and samples were set for sequence analysis.

Expression Refolding and Purification of Compound A

Compound A was expressed in *E-coli* LB21 (λDE3) cells (Novagen®, Madison, Wis. USA) as inclusion bodies. Compound A construct was transformed to *E-coli* cells by heat shock, cells were plated on LBAMP plates and incubated over night at 37° C. Colonies were transferred to rich medium (super broth) supplemented with glucose, $MgSO_4$, AMP and salts. The cells were grown to DO=2 (600 nm) at 37° C., induced with IPTG (final concentration 1 mM) and incubated for an additional 3 h at 37° C.

Inclusion bodies were purified from cell pellet by cell disruption with 0.2 mg/ml of lysozyme followed by the addition of 2.% Triton® X-100 (Octylphenolpoly[ethyleneglycolether]$_x$, Roche Diagnostics GmbH, Roche Applied Science, Mannheim, Germany) and 0.5M NaCl. The pellets of the inclusion bodies were collected by centrifugation (13,000 rpm, 60 min at 4° C.) and washed three times with 50 mM Tris buffer pH 7.4 containing 20 mM EDTA. The isolated and purified inclusion bodies were solubilized in 6M Guanidine HCl pH 7.4, followed by reduction with 65-mM DTE. Solubilized and reduced inclusion bodies were refolded by a 1:100 dilution into a redox-shuffling buffer system containing 0.1-M Tris, 0.001M EDTA, 0.5-M Arginine, and 0.09-mM Oxidized Glutathione, pH 9, and incubation at 10° C. for 24 h. After having been refolded, the protein was dialyzed against 150-mM Urea, 20-mM Tris, pH 8, followed by purification of the soluble Compound A by ionexchange chromatography on a Q-Sepharose® column (7.5 mm I.D 60 cm) (Sigma-Aldrich, Inc., St. Louis, Mo. USA), applying a salt (NaCl) gradient. Peak fractions containing Compound A were then subjected to buffer exchange with PBS.

Cloning of Compound B

The scHLA-A2/SS1 (scFv) was constructed as previously described by linking the C-terminus of scHLA-A2 to the N-terminus of the SS1 scFv via a short linker ASGG (SEQ ID NO:15). To construct the scHLA-A2/SS1 (scFv) with covalently bound MHC-restricted peptide, the MHC-restricted peptide and the peptide linker GGGGSGGGGSGGGGS (SEQ ID NO:8) were fused to the N-terminus of the scHLA-A2/SS1 (scFv) molecule by a PCR overlap extension reaction with the primers 5'-Nde-209B2M: 5'GGAAGCGTTGGCGCATATGATCATGGACCAGGTT CCGTTCTCTGTTGGCGAGGAGGGTCCG-GTGGCGGAGGTTCAGGAGGCGGTG GATCGATC-CAGCGTACTCCAAAG3'(SEQ ID NO: 17) And the 3'VLscSS1-5'GCAGTAAGG AATTCTCAT TATTT-TATTTCCAACTTTGT3'(SEQ ID NO:18). 209cov/scHLA-A2/SS1 (scFv) molecule was used as a template for the construction of Compound B. In this molecule the CMV peptide NLVPMVATV (SEQ ID NO: 4) was introduced into the 209cov/scHLA-A2/SS1 (scFv) sequence (exchanging the 209 peptide) by PCR reaction using the primers 5'GGAAGCGTTGGCGCATATGG GCATTCTGGGCT-TCGTGTTTACCCTGGGCGAGGAGGATC-CGGTGGCGGAGGTTCAGGAGGCGGTGGA TCGATC-CAGCGTACTCCAAAG3'(SEQ ID NO: 17) and the 3'VLscSS15'GCAGTAAGGAATTCTCATTATTTTAT TTCCAACTTTGT3'(SEQ ID NO: 18).

The expression and purification protocols of Compound B were identical to the expression and purification protocols of Compound A.

All the methods used to analyze the biochemical and biological properties of Compound B were identical to the methods used to analyze the activity of Compound A.

Construction of M1-COV/scHLA-A2/SS1 (scFv)

To construct the M1-cov/scHLA-A2/SS1 (scFv) fusion protein the MI 58-66 peptide was fused to the N-terminus of scHLA-A2/SS1 (scFv) fusion protein through a short 15 amino acid linker by overlapping PCR reaction with the 5'M1-linker primer: 5'GGAAGCGTTGGCG-CATATGGGCATTCTGGGCTTCGTGTT-TACCCTGGGCGG AGGAGGATCCGGTGGCGGAGGT-TCAGGAGGCGGTGGATCGATCCAGCGTACTCCAAA-G3'(SEQ ID NO: 13) and the 3'VLscSS1-5'GCAGTAAG-GAATTCTCAT TATTTTATTTCCAACTTTGT3'(SEQ ID NO: 14). PRB plasmid was used as a template containing the scHLA-A2/SS1 (scFv) sequence. The expression and purification protocols of the M1-cov/scHLA-A2/SS1 (scFv) fusion protein were identical to the expression and purification protocols of Compound A. All the methods used to analyse the biochemical and biological properties of the M1-cov/scHLA-A2/SS1 (scFv) fusion protein were identical to the methods used to analyse the activity of Compound A.

Flow Cytometry

Cells were incubated with Compound A (60 min at 4° C. in 100 μl, 10 μg/ml), washed and incubated with the anti-HLA-A2 MAb BB7.2 (60 min at 4° C., 10 μl/ml). The cells were washed and incubated with anti-mouse FITC (60 min at 4° C., 10 μl/ml) that served as a secondary antibody. The cells were subsequently washed and analyzed by a FACS caliber flow cytometer (Becton-Dickinson, San Jose, Calif. USA).

Enzyme Linked Immunosorbent Assay

Immunoplates (Falcon®, Becton-Dickinson Labware, Franklin Lakes, N.J. USA) were coated with 10 μg/ml of purified bacterially produced recombinant mesothelin (O/N at 4° C.). The plates were blocked with PBS containing 2% skim milk and then incubated with various concentrations of Compound A (60 min at RT) and washed three times with PBS. Binding was detected using the anti-HLA-conformational-dependent antibody W6/32 (60 min, RT, 1 μg/ml), plates were washed three times with PBS and incubated with anti-mouse IgG-peroxidase (60 min, RT, 1 μg/ml). The reaction was developed using TMB (DAKO) and terminated by the addition of 50 μl $H_2SO_4$ 2N. Anti-mesothelin antibody (K1) was used as a positive control. The immunoplates were analyzed by ELISA reader using 450 nm filter (Anthos 2001™, Anthos Labtech, Salzburg, Austria).

Cytotoxicity Assays

Cytotoxicity was determined by $S^{35}$-methionine release assays. Target cells were cultured in culture plates in RPMI 10% FCS Methionine free for 2 h, followed by incubation overnight with 15 µCi/ml of $S^{35}$ methionine (NEN). The target cells were harvested by trypsinization and washed twice with 40 ml RPMI 10% FCS. The target cells were plated in 96-well plates ($5 \cdot 10^3$ cells per well) in RMPI+10% FCS and incubated overnight at 37° C., 5% $CO_2$. Target cells were incubated with different concentrations of Compound A fusion proteins for 2 h, effector CTL cells were added at different target: effector ratios and the plates were incubated for 8-12 h at 37° C., 5% $Co_2$. Following incubation, $S^{35}$-methionine release from target cells was measured in a 25 µl sample of the culture supernatant. All assays were performed in triplicate, lysis was calculated directly: ([experimental release–spontaneous release]/[maximum release–spontaneous release])·100. Spontaneous release was measured as $S^{35}$ methionine released from target cells in the absence of effector cells, and maximum release was measured as $S^{35}$-methionine released from target cells lyzed by 0.05M NaOH.

Cell Lines

A431 and A431K5 cells (epidermoid carcinoma) were maintained in RPMI medium containing 10% FCS, L-glutamine and penicillin/streptomycin. The A431K5 cell line is a human epidermoid carcinoma A431 cell line stably transfected with Mesothelin, the transfected cells were maintained with 700 µg/ml G418 (Gibco-BRL®, Invitrogen™ Inc., Carlsbad, Calif. USA).

CTL's with specificity for CMV pp 65 epitope (NLVPMVATV (SEQ ID NO:4)) were kindly provided by Dr Ditmar Zehn (Charitee, Berlin). The CTL's were expanded by incubation with peptide pulsed, radiated (4000rad) PBMC's from a healthy HLA-A2 positive donor and were maintained in AIMV medium+8.9% FCS+50 µM-2-mercaptoethanol+penicillin/streptomycin $1 \cdot 10^5$ U/L.

Results:

Construction of Compound A

A construct encoding a single-chain MHC molecule composed of the β2 microglobulin gene fused to the α1, α2 and α3 of the HLA-A2 gene via a short peptide linker (15 amino acids) was fused to the scFv SS1 which targets mesothelin (FIG. 1A). This construct was analyzed in detail for its biochemical and biological activity and was found to be functional in-vitro and in-vivo (15). To construct a fusion protein with covalently linked peptide a 9 amino acids peptide derived from the CMV pp65 protein (NLVPMVATV) (SEQ ID NO:4) was fused to the N-terminus of the scHLA-A2/SS1 (scFv) fusion protein via 20 amino acids linker GGGGSGGGGSGGGGSGGGGS (SEQ ID NO:6) (FIG. 1B). Compound A was constructed in two steps: First a covalent fusion protein termed M1/scHLA-A2/SS1 (scFv) was constructed by overlap extension PCR. In this construct the influenza M158-66 peptide GILGFVFTL (SEQ ID NO:21) and a 15 amino acid linker were fused to the N-terminus of the scHLA-A2/SS1 (scFv) fusion protein. In this construct, a new, unique restriction site (BamHI) was inserted to the linker sequence by a silent mutation. In the second step PRB plasmid containing the M1/scHLA-A2/SS1 (scFv) full sequence was digested with NdeI and BamHI restriction enzymes. This digestion produced two fragments. One fragment contains the peptide and part of the linker sequence, and the second fragment contains the plasmid, part of the linker and the scHLA-A2/SS1 (scFv) sequence. The fragment which contains the plasmid, part of the linker and the scHLA-A2/SS1 (scFv) sequence was then ligated to dsDNA primer that codes the CMV pp65 peptide sequence and an extension of the linker sequence (FIG. 1B). The new plasmid was transformed to E-coli DH5α cells and positive colonies were sent to DNA sequencing (FIG. 2).

Expression and Purification of Compound A

Compound A was expressed in E. coli BL21 cells and, upon induction with isopropyl β-D-thiogalactoside, large amounts of recombinant protein accumulated in intracellular inclusion bodies. SDS/PAGE analysis of isolated and purified inclusion bodies revealed that Compound A with the correct size constituted 80-90% of the total inclusion bodies mass (FIG. 3A). The isolated solubilized inclusion bodies were reduced and refolded in-vitro in a redox-shuffling buffer. Monomeric soluble fusion proteins (Compound A) were purified by ion-exchange chromatography on Q-sepharose®. SDS/PAGE analysis of Compound A revealed a highly purified monomeric molecule with the expected size of 72 KDa (FIG. 3B).

Biological Activity of the Compound A

ELISA

Figure 4:
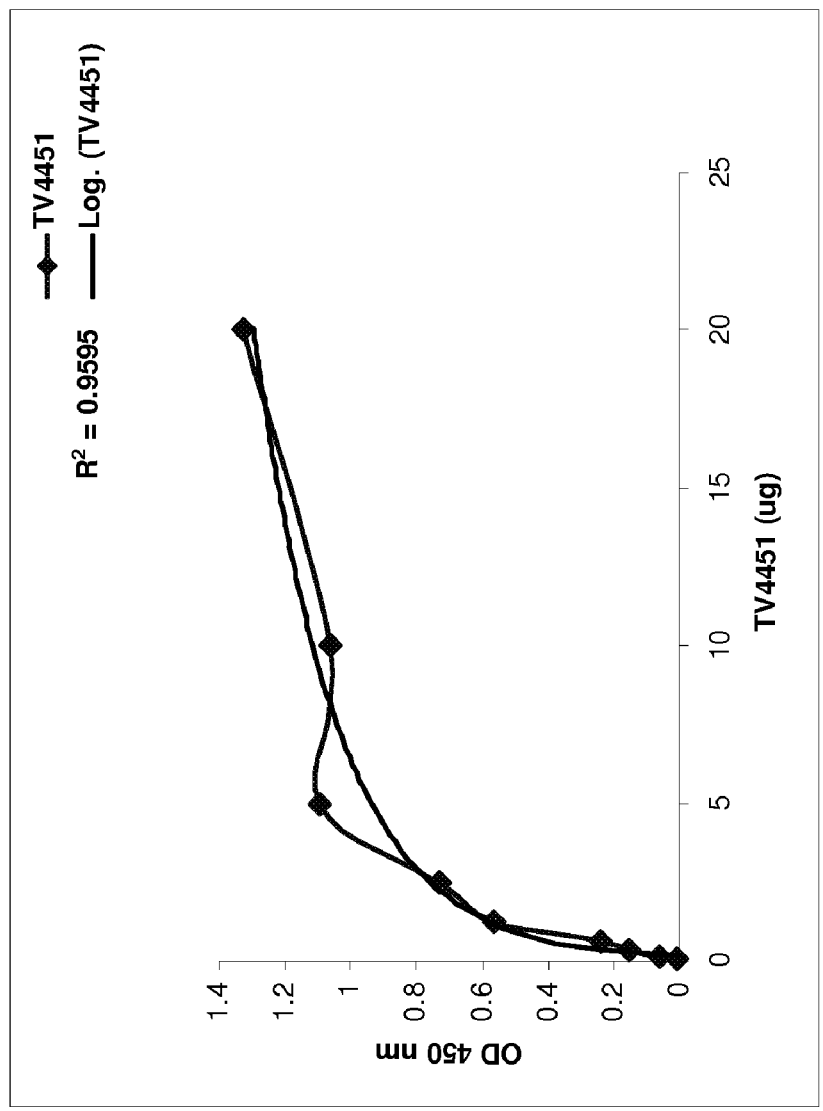

To test the binding ability of purified Compound A to its target antigen, the recombinant mesothelin was immobilized to immunoplates. The binding of Compound A was monitored by using conformation sensitive mAb W6/32, this antibody recognizes MHC molecules that are folded correctly with a peptide in its groove. As shown in FIG. 4, the binding of Compound A to recombinant mesothelin was dose-dependent. This suggests that the two functional domains of Compound A, the scFv (SS1) domain and the peptide/scHLA-A2 domain are folded correctly. Moreover, the scFv (SS1) domain of the fusion protein is in active form and can specifically bind mesothelin.

Flow Cytometry Analysis (FACS)

To test the binding ability of Compound A to mesothelin-expressing cell lines, FACS analysis was made. As a model, target cells that are HLA-A2 negative were used, thus the reactivity of an anti-HLA-A2 mAb can be used to measure the binding of Compound A to cells that express mesothelin on their surface. This model of mesothelin-positive, HLA-A2-negative cells represents the extreme case in which the tumor cells lose its HLA expression. Therefore for the FACS analysis, HLA-A2 negative A431K5 cells were used, which are human epidermoid carcinoma A431 cells that were stably transfected with mesothelin. The parental A431 human epidermoid carcinoma cells which are mesothelin-negative and HLA-A2-negative are used as negative control. The binding of Compound A to the target cells was monitored with anti-HLA-A2 mAb BB7.2 as primary antibody followed by a FITC labeled secondary antibody. A mesothelin anti-mAb K1 was used to test the expression levels of mesothelin. As shown in FIG. 5A, A431K5 cells express high levels of mesothelin, whereas the parental A431 cells do not express the target antigen. The cell lines A431 and A431K5 were also tested for the expression of HLA-A2 using HLA-A2 specific antibody (BB7.2), both cell lines were HLA-A2 negative. However, when A431K5 cells were pre-incubated with Compound A, they were positively stained with the HLA-A2 specific antibody BB7.2 (FIG. 5B). Antigen-negative A413 cells were not affected. The specific binding of Compound A to A431K5 but not to A431 cells further indicates that the binding is exclusively depended on the interaction of the targeting scFv domain of the fusion with mesothelin and that the fusion protein can bind its target antigen as natively expressed on the surface of cells.

Cytotoxicity Assay

To test the ability of Compound A to mediate the killing of HLA-A2-negative mesothelin-positive cells by HLA-A2-restricted CMV pp 65 NLVPMVATV (SEQ ID NO:4) specific CTLs, $S^{35}$-Methionine release assay was performed using HLA-A2-negative mesothelin-transfected A431K5 cells, and the HLA-A2-negative mesothelin-negative A431 parental cells. To determine the killing potential of the CMV specific CTLs, cytotoxicity assay was performed using HLA-A2-positive JY cells that were radiolabeled with MetS$^{35}$ and laded with the CMV peptide NLVPMVATV (SEQ ID NO:4). The average specific killing of the JY cells by the CMV specific CTLs was 47% with an E:T ratio of 10:1 (data not shown). As shown in FIG. 6a, Compound A effectively mediated the killing of the A431K5 cells (mesothelin-positive HLA-A2-negative). Specific killing could reach 66% in comparison to peptide-loaded JY cells. Thus, killing with the fusion protein was even more efficient compared to peptide-pulsed antigen presenting cells which represent optimal targets. However, when the target A431K5 cells were incubated with the CMV specific CTLs alone without preincubation with Compound A or when the target cells were A431 mesothelin-negative cells with or without preincubation with Compound A, no cytotoxic activity was observed. Next, a titration experiment was performed to determine the potency of Compound A, as shown in FIG. 6b, the killing of mesothelin-positive A431K5 cells was dose-dependent with an IC50 of 0.5-1 µg/ml.

These results indicate that the killing of mesothelin-positive HLA-A2-negative A431K5 cell was specific and controlled by the recognition of mesothelin by the targeting domain of Compound A (scFv/SS1) and the specificity of the CMV CTLs to the peptide/scHLA-A2 domain.

Biological Activity of Compound B
Flow Cytometry Analysis (FACS)

To test the binding ability of Compound B to mesothelin-expressing cell lines a flow cytometry analysis was used. As a model, target cells that are HLA-A2 negative were used, thus, the reactivity of the anti-HLA-A2 mAb will indicate the binding of Compound B to the cell surface antigen. A431K5 cells which are human epidermoid carcinoma A431 cells that were stably transfected with mesothelin and are HLA-A2 negative. As controls the parental A431 human epidermoid carcinoma cells were used which are mesothelin-negative and HLA-A2 negative. The binding of Compound B to the target cells was monitored by anti-HLA-A2 mAb BB7.2 as primary antibody followed by a FITC labeled secondary antibody. To test the expression levels of mesothelin and as positive control a commercial anti-mesothelin mAb K1 was used. As shown in FIG. 10A-B A431K5 cells express high levels of mesothelin, whereas the parental A431 cells do not express mesothelin. The cell lines A431 and A431K5 were also tested for their expression of HLA-A2 using HLA-A2 specific anti body (BB7.2), both cell lines were HLA-A2 negative. However, when A431K5 cells were pre-incubated with Compound B, they were positively stained with the HLA-A2 specific antibody BB7.2 whereas control A431 cells were not stained (FIG. 10C-D). The specific binding of Compound B to A431K5 cells but not to A431 cells indicate that binding is exclusively depended on the interaction of the targeting scFv domain with mesothelin.

To analyze the binding of Compound B in comparison to the Compound A fusion, a FACS analysis was performed using both molecules in similar conditions and concentrations. As shown in FIGS. 10E-F only the mesothelin-positive cells A431K5 were positively stained with HLA-A2-specific Ab when pre-incubated with both fusion proteins, however, Compound A exhibited better binding.

Cytotoxicity Assay

Figure 12:
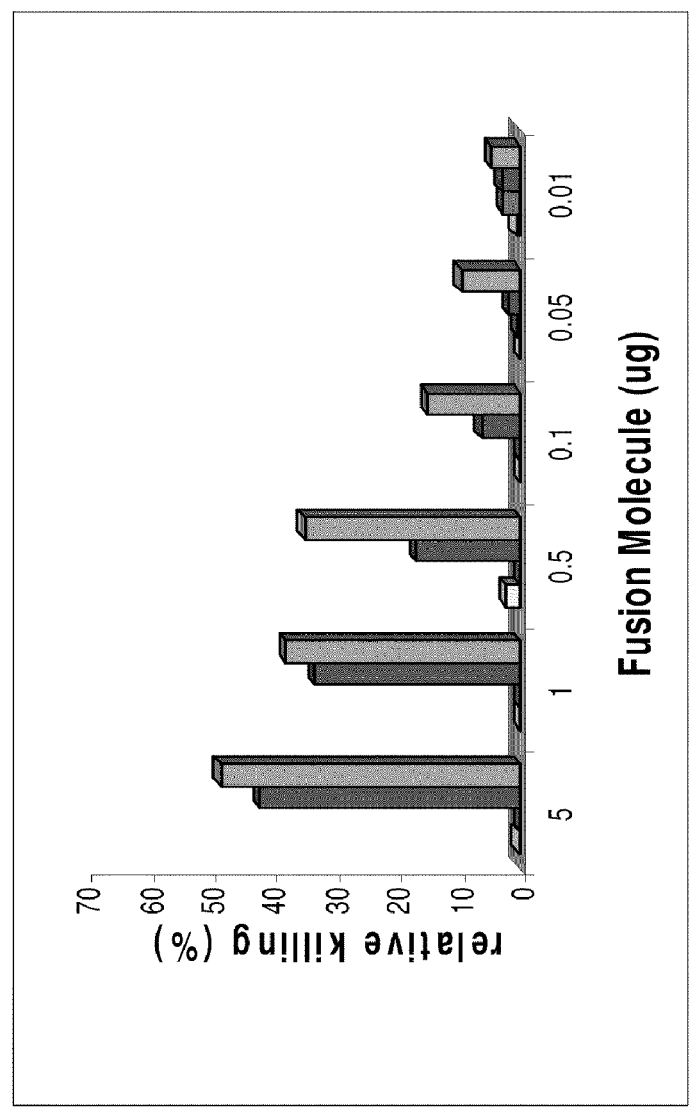

To test the ability of Compound B to mediate the killing of HLA-A2-negative mesothelin-positive cells by HLA-A2-restricted CMV NLVPMVATV (SEQ ID NO:4) specific CTLs, performed $S^{35}$-Methionine release assay using HLA-A2-negative mesothelin-transfected A431K5 cells was performed, and the HLA-A2-negative mesothelin-negative A431 parental cells. To determine the killing potential of the CMV-specific CTLs cytotoxicity assay was performed, using HLA-A2-positive JY cells that were radiolabeled with MetS$^{35}$ and laded with the CMV peptide NLVPMVATV (SEQ ID NO: 4). The average specific killing of the JY cells by the CMV-specific CTLs was around 45-50% using an E:T ratio of 10:1 (data not shown). As shown in FIG. 11A, Compound B effectively mediated the killing of the A431K5 cells (mesothelin-positive HLA-A2-negative), this specific killing was 66% in comparison with peptide-loaded JY cells (~150% compared to JY cells). However, when the target A431K5 cells were incubated with the CMV-specific CTLs alone without preincubation with Compound B or when the target cells were mesothelin-negative (A431 cells), with or without preincubation with Compound B, no cytotoxic activity was observed. Titration experiments which determined the potency of the fusion protein, shown in FIG. 11B indicate that the killing of mesothelin-positive A431K5 cells was dose-dependent. To compare the cytotoxic activity of Compound B and Compound A fusion proteins, which differ in the length of peptide used to covalently attach the antigenic peptide to the β-2 microglobulin, a $S^{35}$-Methionine release assay was performed using similar conditions for both fusion proteins. As shown in FIG. 12, both molecules efficiently and specifically mediated the killing of A431K5 cells, but not A431 cells. When relatively high concentrations of fusion proteins (Compound B and Compound A) were used, the killing activity of both molecules was similar. However, when low concentrations of fusion proteins were used the cytotoxic activity of Compound A was superior probably due to better stability and positioning of the CMV peptide in the MHC peptide-binding groove due to the longer linker.

M1-COV/scHLA-A2/SS1

The M1-cov/scHLA-A2/SS1 (scFv) fusion protein was constructed by overlap extension PCR reaction in which the Influenza M1 58-66 peptide and a 15 amino acid linker GGGGSGGGGSGGGGS were fused to the N-terminus of the scHLA-A2/SS1 (scFv) fusion protein (FIG. 13). The PCR product was ligated to TA-cloning vector (p-GEM, Promega), transformed to *E-coli* DH5α cells. Positive colonies were selected and the insert was isolated using EcoRI and NdeI. The insert was ligated to PRB expression vector and transformed to *E-coli* DH5α cells. Positive colonies were sent to DNA sequencing (FIG. 14).

Expression and Purification of Compound B

The M1-cov/scHLA-A2/SS1 (scFv) fusion protein was expressed in *E. coli* BL21 cells and, upon induction with isopropyl β-D-thiogalactoside, large amounts of recombinant protein accumulated in intracellular inclusion bodies. SDS/PAGE analysis of isolated and purified inclusion bodies revealed that the M1-cov/scHLA-A2/SS1 (scFv) fusion protein with the correct size constituted 80-90% of the total inclusion bodies mass (FIG. 15A). The isolated solubilized inclusion bodies were reduced and refolded in vitro in a redox-shuffling buffer. Monomeric soluble fusion proteins (M1-cov/scHLA-A2/SS1 (scFv)) were purified by ion-exchange chromatography on Q-sheparose. SDS/PAGE analysis of the M1-cov/scHLA-A2/SS1 (scFv) fusion proteins revealed a highly purified monomeric molecule with the expected size of 72 KDa (FIG. 15B).

ELISA

Figure 16:
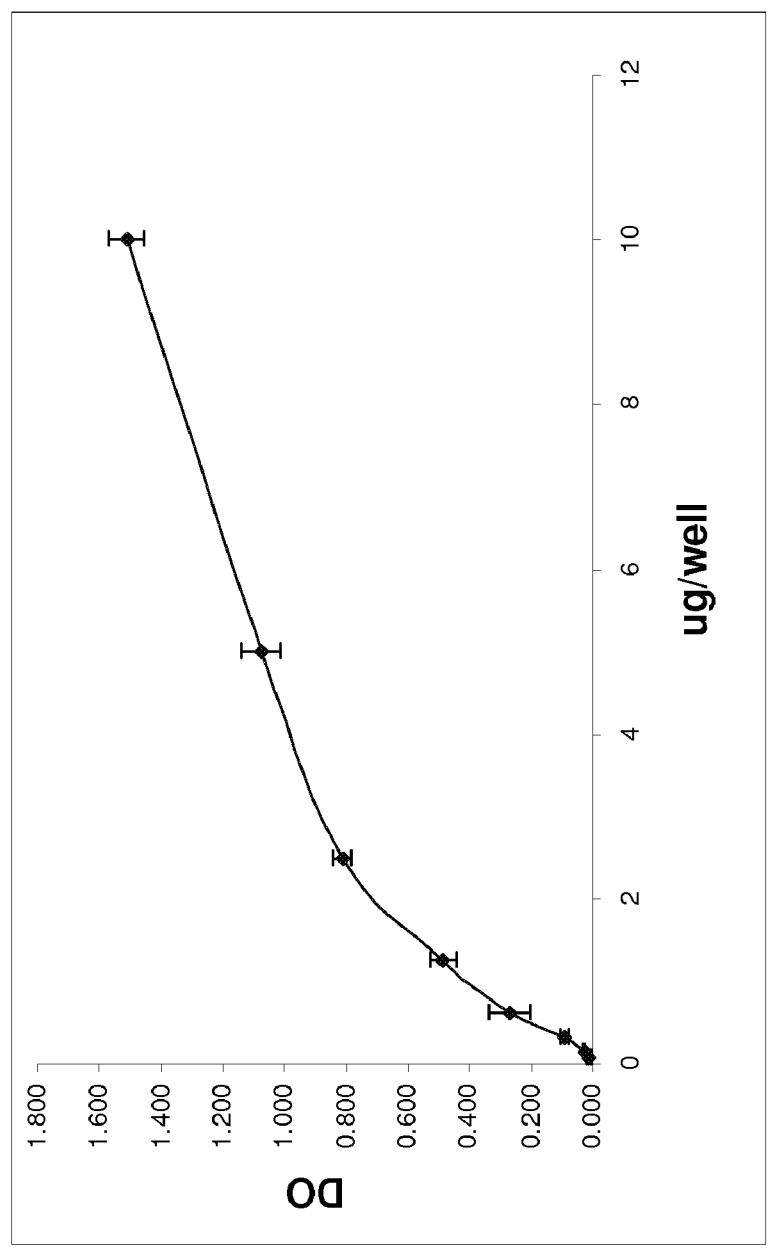

To test the binding ability of the purified M1-cov/scHLA-A2/SS1 (scFv) fusion protein to it target antigen, recombinant mesothelin was immobilized to immunoplates. The binding of M1-cov/scHLA-A2/SS1 (scFv) fusion protein was monitored by using conformation sensitive mAb W6/32, this antibody recognizes MHC molecules that are folded correctly with a peptide in its groove. As shown in FIG. 16 the binding of the M1-cov/scHLA-A2/SS1 (scFv) fusion protein to recombinant mesothelin was dose-dependent. This suggests that the two functional domains of M1-cov/scHLA-A2/SS1 (scFv) fusion protein, the scFv (SS1) domain and the M1-cov/scHLA-A2 domain are folded correctly. Moreover, the scFv (SS1) domain of the fusion protein is in active form and can specifically bind mesothelin.

Flow Cytometry Analysis (FACS)

To test the binding ability of the M1-cov/scHLA-A2/SS1 (scFv) fusion protein to mesothelin-expressing cell lines, FACS analysis was used. As a model, target cells that are HLA-A2-negative were used, and the anti-HLA-A2 mAb can be used to monitor the binding of the M1-cov/scHLA-A2/SS1 (scFv) fusion protein to the cell surface antigen. For the FACS analysis, the mesothelin-transfected A431K5 cells were used. The binding of the M1-cov/scHLA-A2/SS1 (scFv) fusion protein to the target cells was monitored by anti-HLA-A2 mAb BB7.2 as primary antibody followed by a FITC-labeled secondary antibody. To test the expression levels of mesothelin and as positive control, a commercial anti mesothelin mAb K1 was used. As shown in FIG. 17A-B, A431K5 cells express high levels of mesothelin, whereas the parental A431 cells do not express mesothelin. The cell lines A431 and A431K5 were also tested for their expression of HLA-A2 using HLA-A2 specific antibody (BB7.2), both cell lines were HLA-A2-negative. However, when A431K5 cells but not A431 cells were pre-incubated with the M1-cov/scHLA-A2/SS1 (scFv) fusion proteins, they were positively stained with the HLA-A2-specific antibody BB7.2 (FIG. 17C-D). This specific binding of the M1-cov/scHLA-A2/SS1 (scFv) fusion protein to A431K5 cells and not to A431 cells indicates that the binding is exclusively dependent on the interaction of the targeting domain (scFv(SS1)) with mesothelin.

Cytotoxicity Assay

To test the ability of the M1-cov/scHLA-A2/SS1 (scFv) fusion protein to mediate the killing of HLA-A2-negative mesothelin-positive cells by HLA-A2-restrictive M158-66 specific CTLs, $S^{35}$-Methionine release assay using HLA-A2-negative mesothelin-transfected A431K5 cells was performed. As shown in FIG. 18, M1-cov/scHLA-A2/SS1 (scFv) fusion protein did not mediate the lysis of A431K5 cells (mesothelin-positive HLA-A2-negative). However, the scHLA-A2/SS1 (scFv) bearing the M158-66 peptide in its groove mediated the killing of mesothelin-positive target cells by the HLA-A2-restricted M158-66 specific CTLs.

Discussion

This study demonstrates the ability to target covalently linked peptide/scMHC/scFv fusion protein to tumor cells can render HLA-A2-negative cells susceptible to lysis by the relevant HLA-A2-restricted CTLs. As previously shown by Lev et al., and Oved et al. (15, 21), this strategy has two major advantages. First, it takes advantage of the use of recombinant Ab fragments that can localize on those malignant cells that express a tumor marker, usually associated with the transformed phenotype (such as growth factor receptors and/or differentiation antigens), with a relatively high degree of specificity. Second, this strategy has the ability to recruit a particular population of highly reactive cytotoxic T-cells specific to a preselected, highly antigenic peptide epitope present in the targeted MHC-peptide complex, such as viral-specific T-cell epitopes. This platform approach generates multiple molecules with many tumor-specific scFv fragments that target various tumor specific antigens, combined with the ability to target many types of MHC-peptide complexes carrying single, preselected, and highly antigenic peptides derived from tumor, viral, or bacterial T-cell epitopes. These examples present a strategy one step farther by fusing the 9 amino acid peptide linked by a short linker (20AA) to the previously reported scHLA-A2/scFv fusion protein (15AA), and by doing so, stabilizing the peptide in the MHC groove prolonging the general stability of the fusion proteins. As a model for this new generation of fusion proteins, the present invention relates to construction of a fusion protein in which the CMV pp65 derived (NLVPMVATV) fused to the N-terminus of the scHLA-A2/SS1 (scFv) molecule and its biochemical and biological characteristics. It is shown that the two domains of the new fusion protein can refold in vitro to form correctly folded molecules with the peptide within the HLA-A2 groove and an active targeting domain (scFv) that can specifically bind its target antigen. Moreover, this fusion protein had successfully mediated the lysis of HLA-A2-negative mesothelin-positive tumor cells by HLA-A2-restricted CTLs.

Tumor progression is often associated with the secretion of immune-suppressive factors and/or the down-regulation of MHC class I antigen-presentation functions (2). Even when a specific CTL response is demonstrated in patients, this response is low because the anti-tumor CTL population is rare, very infrequent, and in some cases the CLTs are not functional or anergic (26). Moreover, it is well-established that the number of MHC-peptide complexes on the surface of tumor cells that present a particular tumor-associated peptide is low (27). As shown herein, the new strategy overcame these problems. First, the tumor cells are coated with MHC-peptide complexes independent of their endogenous MHC expression. Second, the use of tumor specific antigens that are usually part of the tumor phenotype (such as growth factor receptors and differentiation antigens) prevent the down regulation of those antigens and prolong the efficiency of the treatment. Third and most important, the effector domain of the fusion protein the MHC-peptide complex can recruit specific populations of CTLs depending on the peptide harboring the MHC groove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCE CITED

1. Gilboa, E. How tumors escape immune destruction and what we can do about it. Cancer Immunol. Immunother. 48, 382-385 (1999).
2. Seliger, B., Maeurer, M. J., & Ferrone, S. Antigen-processing machinery breakdown and tumor growth. Immunol. Today 21, 455-464 (2000).
3. Garcia-Lora, A., Algarra, I., & Garrido, F. MHC class I antigens, immune surveillance, and tumor immune escape. J. Cell Physiol 195, 346-355 (2003).
4. Garrido, F. & Algarra, I. MHC antigens and tumor escape from immune surveillance. Adv. Cancer Res. 83, 117-158 (2001).
5. McLaughlin, P. et al. Rituximab chimeric anti-CD20 monoclonal antibody therapy for relapsed indolent lymphoma: half of patients respond to a four-dose treatment program. J. Clin. Oncol. 16, 2825-2833 (1998).
6. Cobleigh, M. A. et al. Multinational study of the efficacy and safety of humanized anti-HER2 monoclonal antibody in women who have HER2-overexpressing metastatic breast cancer that has progressed after chemotherapy for metastatic disease. J. Clin. Oncol. 17, 2639-2648 (1999).
7. Pastan, I. & Kreitman, R. J. Immunotoxins in cancer therapy. Curr. Opin. Investig. Drugs 3, 1089-1091 (2002).
8. Boon, T. & van der, B. P. Human tumor antigens recognized by T-lymphocytes. J. Exp. Med. 183, 725-729 (1996).
9. Esche, C., Shurin, M. R., & Lotze, M. T. The use of dendritic cells for cancer vaccination. Curr. Opin. Mol. Ther. 1, 72-81 (1999).
10. Offringa, R., van der Burg, S. H., Ossendorp, F., Toes, R. E., & Melief, C. J. Design and evaluation of antigen-specific vaccination strategies against cancer. Curr. Opin. Immunol. 12, 576-582 (2000).
11. Wang, E., Phan, G. Q., & Marincola, F. M. T-cell-directed cancer vaccines: the melanoma model. Expert. Opin. Biol. Ther. 1, 277-290 (2001).
12. Dudley, M. E. et al. Cancer regression and autoimmunity in patients after clonal repopulation with antitumor lymphocytes. Science 298, 850-854 (2002).
13. Dudley, M. E. & Rosenberg, S. A. Adoptive-cell-transfer therapy for the treatment of patients with cancer. Nat. Rev. Cancer 3, 666-675 (2003).
14. Rosenberg, S. A. Progress in human tumour immunology and immunotherapy. Nature 411, 380-384 (2001).
15. Lev, A. et al. Tumor-specific Ab-mediated targeting of MHC-peptide complexes induces regression of human tumor xenografts in vivo. Proc. Natl. Acad. Sci. U.S.A 101, 9051-9056 (2004).
16. Donda, A. et al. In vivo targeting of an anti-tumor antibody coupled to antigenic MHC class I complexes induces specific growth inhibition and regression of established syngeneic tumor grafts. Cancer Immun. 3, 11 (2003).
17. Ogg, G. S. et al. Sensitization of tumour cells to lysis by virus-specific CTL using antibody-targeted MHC class I/peptide complexes. Br. J. Cancer 82, 1058-1062 (2000).
18. Robert, B., Guillaume, P., Luescher, I., Romero, P., & Mach, J. P. Antibody-conjugated MHC class I tetramers can target tumor cells for specific lysis by T-lymphocytes. Eur. J. Immunol. 30, 3165-3170 (2000).
19. Robert, B. et al. Redirecting anti-viral CTL against cancer cells by surface targeting of monomeric MHC class I-viral peptide conjugated to antibody fragments. Cancer Immun. 1, 2 (2001).
20. Savage, P. et al. Anti-viral cytotoxic T-cells inhibit the growth of cancer cells with antibody targeted HLA class I/peptide complexes in SCID mice. Int. J. Cancer 98, 561-566 (2002).
21. Oved, K., Lev, A., Noy, R., Segal, D., & Reiter, Y. Antibody-mediated targeting of human single-chain class I MHC with covalently linked peptides induces efficient killing of tumor cells by tumor or viral-specific cytotoxic T-lymphocytes. Cancer Immunol. Immunother. 54, 867-879 (2005).
22. Chang, K. & Pastan, I. Molecular cloning and expression of a cDNA encoding a protein detected by the K1 antibody from an ovarian carcinoma (OVCAR-3) cell line. Int. J. Cancer 57, 90-97 (1994).
23. Chang, K. & Pastan, I. Molecular cloning of mesothelin, a differentiation antigen present on mesothelium, mesotheliomas, and ovarian cancers. Proc. Natl. Acad. Sci. U.S.A 93, 136-140 (1996).
24. Chang, K. & Pastan, I. Molecular cloning of mesothelin, a differentiation antigen present on mesothelium, mesotheliomas, and ovarian cancers. Proc. Natl. Acad. Sci. U.S.A 93, 136-140 (1996).
25. Hassan, R., Bera, T., & Pastan, I. Mesothelin: a new target for immunotherapy. Clin. Cancer Res. 10, 3937-3942 (2004).
26. Lee, P. P. et al. Characterization of circulating T-cells specific for tumor-associated antigens in melanoma patients. Nat. Med. 5, 677-685 (1999).
27. Christinck, E. R., Luscher, M. A., Barber, B. H., & Williams, D. B. Peptide binding to class I MHC on living cells and quantitation of complexes required for CTL lysis. Nature 352, 67-70 (1991).
28. Jain, R. K. Transport of molecules, particles, and cells in solid tumors. Annu. Rev. Biomed. Eng 1, 241-263 (1999).
29. Bromley, S. K. et al. The immunological synapse. Annu. Rev. Immunol. 19, 375-396 (2001).
30. Lanzavecchia, A., Lezzi, G., & Viola, A. From TCR engagement to T-cell activation: a kinetic view of T-cell behavior. Cell 96, 1-4 (1999).
31. Chang, K., Pastan, I. & Willingham, M. C. Isolation and characterization of a monoclonal antibody, K1, reactive with ovarian cancers and normal mesothelium. *Int. J. Cancer* 50, 373-381 (1992).
32. Chang, K., Pai, L. H., Batra, J. K., Pastan, I. & Willingham, M. C. Characterization of the antigen (CAK1) recognized by monoclonal antibody K1 present on ovarian cancers and normal mesothelium. *Cancer Res.* 52, 181-186 (1992).
33. Parham, P., Barnstable, C. J. & Bodmer, W. F. Use of a monoclonal antibody (W6/32) in structural studies of HLA-A,B,C, antigens. *J. Immunol.* 123, 342-349 (1979).
34. Shields, M. J. & Ribaudo, R. K. Mapping of the monoclonal antibody W6/32: sensitivity to the amino terminus of beta2-microglobulin. *Tissue Antigens* 51, 567-570 (1998).
35. Parham, P. & Brodsky, F. M. Partial purification and some properties of BB7.2. A cytotoxic monoclonal antibody with specificity for HLA-A2 and a variant of HLA-A28. *Hum. Immunol.* 3, 277-299 (1981).

What is claimed:

1. A fusion protein comprising the amino acid sequence set forth in SEQ ID NO: 2.

\* \* \* \* \*

SEQUENCE LISTING

<160> NUMBER OF SEQ ID NOS: 23

<210> SEQ ID NO 1
<211> LENGTH: 1995
<212> TYPE: DNA
<213> ORGANISM: artificial sequence
<220> FEATURE:
<223> OTHER INFORMATION: Compound A fusion protein

<400> SEQUENCE: 1

```
atgaacctgg tgccgatggt cgcgaccgtt ggaggtggcg gttctggcgg aggaggatcc     60
ggtggcggag gttcaggagg cggtggatcg atccagcgta ctccaaagat tcaggtttac    120
tcacgtcatc cagcagagaa tggaaagtca aatttcctga attgctatgt gtctgggttt    180
catccatccg acattgaagt tgacttactg aagaatggag agagaattga aaaagtggag    240
cattcagact tgtctttttc gaaggactgg tctttctatc tcttgtacta cactgaattc    300
accccccactg aaaaagatga gtatgcctgc cgtgtgaacc atgtgacttt gtcacagccc    360
aagatagtta agtgggatcg cgacatgggt ggcggtggaa gcggcggtgg aggctctggt    420
ggaggtggca gcggctctca ctccatgagg tatttcttca catccgtgtc ccggcccggc    480
cgcggggagc cccgcttcat cgcagtgggc tacgtggacg acacgcagtt cgtgcggttc    540
gacagcgacg ccgcgagcca aggatggag ccgcgggcgc cgtggataga gcaggagggt    600
ccggagtatt gggacgggga gacacggaaa gtgaaggccc actcacagac tcaccgagtg    660
gacctgggga ccctgcgcgg ctactacaac agagcgaggc ccggttctca caccgtccag    720
aggatgtatg gctgcgacgt ggggtcgac tggcgcttcc tccgcgggta ccaccagtac    780
gcgtacgacg gcaaggatta catcgccctg aaagaggacc tgcgctcttg gaccgcggcg    840
gacatggcag ctcagaccac caagcacaag tgggaggcgg cccatgtagc ggagcagttg    900
agagcctacc tggagggcac gtgcgtggag tggctccgca gatacctgga gaacgggaag    960
gagacgctgc agcgcacgga cgccccccaaa acgcacatga ctcaccacgc tgtctctgac   1020
catgaagcca ccctgaggtg ctgggccctg agcttctacc ctgcggagat cacactgacc   1080
tggcagcggg atgggaggga ccagacccag gacacggagc tcgtggagac aaggcctgca   1140
ggggatggaa ccttccagaa gtgggcggct gtggtggtgc cttctggaca ggagcagaga   1200
tacacctgcc atgtgcagca tgagggtttg cccaagcccc tcaccctgag atgggaggct   1260
tccggaggtc aggtacaact gcagcagtct gggcctgagc tggagaagcc tggcgcttca   1320
gtgaagatat cctgcaaggc ttctggttac tcattcactg gctacaccat gaactgggtg   1380
aagcagagcc atgaaagag ccttgagtgg attggactta ttactcctta caatggtgct   1440
tctagctaca accagaagtt caggggcaag gccacattaa ctgtagacaa gtcatccagc   1500
acagcctaca tggacctcct cagtctgaca tctgaagact ctgcagtcta tttctgtgca   1560
agggggggtt acgacgggag gggttttgac tactggggcc aagggaccac ggtcaccgtc   1620
tcctcaggtg taggcggttc aggcggcggt ggctctggcg gtgcggatc ggacatcgag   1680
ctcactcagt ctccagcaat catgtctgca tctccagggg agaaggtcac catgacctgc   1740
agtgccagct caagtgtaag ttacatgcac tggtaccagc agaagtcagg cacctccccc   1800
aaaagatgga tttatgacac atccaaactg gcttctggag tcccaggtcg cttcagtggc   1860
agtgggtctg gaaactctta ctctctcaca atcagcagcg tggaggctga agatgatgca   1920
acttattact gccagcagtg gagtaagcac cctctcacgt tcggtgctgg gacaaagttg   1980
```

-continued gaaataaaat aatga                                                                1995

<210> SEQ ID NO 2
<211> LENGTH: 663
<212> TYPE: PRT
<213> ORGANISM: artificial sequence
<220> FEATURE:
<223> OTHER INFORMATION: Compound A fusion protein

<400> SEQUENCE: 2

```
Met Asn Leu Val Pro Met Val Ala Thr Val Gly Gly Gly Ser Gly
 1               5                  10                  15

Gly Gly Gly Ser Gly Gly Gly Ser Gly Gly Gly Ser Ile Gln
             20                  25                  30

Arg Thr Pro Lys Ile Gln Val Tyr Ser Arg His Pro Ala Glu Asn Gly
             35                  40                  45

Lys Ser Asn Phe Leu Asn Cys Tyr Val Ser Gly Phe His Pro Ser Asp
         50                  55                  60

Ile Glu Val Asp Leu Leu Lys Asn Gly Glu Arg Ile Glu Lys Val Glu
65                  70                  75                  80

His Ser Asp Leu Ser Phe Ser Lys Asp Trp Ser Phe Tyr Leu Leu Tyr
                 85                  90                  95

Tyr Thr Glu Phe Thr Pro Thr Glu Lys Asp Glu Tyr Ala Cys Arg Val
            100                 105                 110

Asn His Val Thr Leu Ser Gln Pro Lys Ile Val Lys Trp Asp Arg Asp
            115                 120                 125

Met Gly Gly Gly Ser Gly Gly Gly Ser Gly Gly Gly Ser
            130                 135                 140

Gly Ser His Ser Met Arg Tyr Phe Phe Thr Ser Val Ser Arg Pro Gly
145                 150                 155                 160

Arg Gly Glu Pro Arg Phe Ile Ala Val Gly Tyr Val Asp Asp Thr Gln
                165                 170                 175

Phe Val Arg Phe Asp Ser Asp Ala Ala Ser Gln Arg Met Glu Pro Arg
            180                 185                 190

Ala Pro Trp Ile Glu Gln Glu Gly Pro Glu Tyr Trp Asp Gly Glu Thr
            195                 200                 205

Arg Lys Val Lys Ala His Ser Gln Thr His Arg Val Asp Leu Gly Thr
            210                 215                 220

Leu Arg Gly Tyr Tyr Asn Gln Ser Glu Ala Gly Ser His Thr Val Gln
225                 230                 235                 240

Arg Met Tyr Gly Cys Asp Val Gly Ser Asp Trp Arg Phe Leu Arg Gly
                245                 250                 255

Tyr His Gln Tyr Ala Tyr Asp Gly Lys Asp Tyr Ile Ala Leu Lys Glu
            260                 265                 270

Asp Leu Arg Ser Trp Thr Ala Ala Asp Met Ala Ala Gln Thr Thr Lys
            275                 280                 285

His Lys Trp Glu Ala Ala His Val Ala Glu Gln Leu Arg Ala Tyr Leu
            290                 295                 300

Glu Gly Thr Cys Val Glu Trp Leu Arg Arg Tyr Leu Glu Asn Gly Lys
305                 310                 315                 320

Glu Thr Leu Gln Arg Thr Asp Ala Pro Lys Thr His Met Thr His His
                325                 330                 335

Ala Val Ser Asp His Glu Ala Thr Leu Arg Cys Trp Ala Leu Ser Phe
            340                 345                 350

Tyr Pro Ala Glu Ile Thr Leu Thr Trp Gln Arg Asp Gly Glu Asp Gln
            355                 360                 365
```

Thr Gln Asp Thr Glu Leu Val Glu Thr Arg Pro Ala Gly Asp Gly Thr
            370                 375                 380

Phe Gln Lys Trp Ala Ala Val Val Pro Ser Gly Gln Glu Gln Arg
385                 390                 395                 400

Tyr Thr Cys His Val Gln His Glu Gly Leu Pro Lys Pro Leu Thr Leu
                405                 410                 415

Arg Trp Glu Ala Ser Gly Gly Gln Val Gln Leu Gln Gln Ser Gly Pro
            420                 425                 430

Glu Leu Glu Lys Pro Gly Ala Ser Val Lys Ile Ser Cys Lys Ala Ser
            435                 440                 445

Gly Tyr Ser Phe Thr Gly Tyr Thr Met Asn Trp Val Lys Gln Ser His
        450                 455                 460

Gly Lys Ser Leu Glu Trp Ile Gly Leu Ile Thr Pro Tyr Asn Gly Ala
465                 470                 475                 480

Ser Ser Tyr Asn Gln Lys Phe Arg Gly Lys Ala Thr Leu Thr Val Asp
                485                 490                 495

Lys Ser Ser Ser Thr Ala Tyr Met Asp Leu Leu Ser Leu Thr Ser Glu
            500                 505                 510

Asp Ser Ala Val Tyr Phe Cys Ala Arg Gly Gly Tyr Asp Gly Arg Gly
            515                 520                 525

Phe Asp Tyr Trp Gly Gln Gly Thr Thr Val Thr Val Ser Ser Gly Val
        530                 535                 540

Gly Gly Ser Gly Gly Gly Gly Ser Gly Gly Gly Ser Asp Ile Glu
545                 550                 555                 560

Leu Thr Gln Ser Pro Ala Ile Met Ser Ala Ser Pro Gly Glu Lys Val
                565                 570                 575

Thr Met Thr Cys Ser Ala Ser Ser Ser Val Ser Tyr Met His Trp Tyr
            580                 585                 590

Gln Gln Lys Ser Gly Thr Ser Pro Lys Arg Trp Ile Tyr Asp Thr Ser
        595                 600                 605

Lys Leu Ala Ser Gly Val Pro Gly Arg Phe Ser Gly Ser Gly Ser Gly
610                 615                 620

Asn Ser Tyr Ser Leu Thr Ile Ser Ser Val Glu Ala Glu Asp Asp Ala
625                 630                 635                 640

Thr Tyr Tyr Cys Gln Gln Trp Ser Lys His Pro Leu Thr Phe Gly Ala
                645                 650                 655

Gly Thr Lys Leu Glu Ile Lys
            660

<210> SEQ ID NO 3
<211> LENGTH: 27
<212> TYPE: DNA
<213> ORGANISM: artificial sequence
<220> FEATURE:
<223> OTHER INFORMATION: CMV peptide

<400> SEQUENCE: 3
aacctggtgc cgatggtcgc gaccgtt                                         27

<210> SEQ ID NO 4
<211> LENGTH: 9
<212> TYPE: PRT
<213> ORGANISM: artificial sequence
<220> FEATURE:
<223> OTHER INFORMATION: CMV peptide

<400> SEQUENCE: 4

Asn Leu Val Pro Met Val Ala Thr Val
1               5

<210> SEQ ID NO 5
<211> LENGTH: 60
<212> TYPE: DNA
<213> ORGANISM: artificial sequence
<220> FEATURE:
<223> OTHER INFORMATION: 20-aa peptide linker

<400> SEQUENCE: 5
ggaggtggcg gttctggcgg aggaggatcc ggtggcggag gttcaggagg cggtggatcg        60

<210> SEQ ID NO 6
<211> LENGTH: 20
<212> TYPE: PRT
<213> ORGANISM: artificial sequence
<220> FEATURE:
<223> OTHER INFORMATION: 20-aa peptide linker

<400> SEQUENCE: 6

Gly Gly Gly Gly Ser Gly Gly Gly Ser Gly Gly Gly Gly Ser Gly
1               5                   10                  15

Gly Gly Gly Ser
            20

<210> SEQ ID NO 7
<211> LENGTH: 45
<212> TYPE: DNA
<213> ORGANISM: artificial sequence
<220> FEATURE:
<223> OTHER INFORMATION: 15-aa peptide linker

<400> SEQUENCE: 7
ggtggcggtg gaagcggcgg tggaggctct ggtggaggtg gcagc                        45

<210> SEQ ID NO 8
<211> LENGTH: 15
<212> TYPE: PRT
<213> ORGANISM: artificial sequence
<220> FEATURE:
<223> OTHER INFORMATION: 15-aa peptide linker

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 12
<212> TYPE: DNA
<213> ORGANISM: artificial sequence
<220> FEATURE:
<223> OTHER INFORMATION: 4-aa peptide linker

<400> SEQUENCE: 9
gcttccggag gt                                                             12

<210> SEQ ID NO 10
<211> LENGTH: 4
<212> TYPE: PRT
<213> ORGANISM: artificial sequence
<220> FEATURE:
<223> OTHER INFORMATION: 4-aa peptide linker

<400> SEQUENCE: 10

Ala Ser Gly Gly
1

<210> SEQ ID NO 11
<211> LENGTH: 726
<212> TYPE: DNA
<213> ORGANISM: artificial sequence
<220> FEATURE:
<223> OTHER INFORMATION: SS1

<400> SEQUENCE: 11

```
caggtacaac tgcagcagtc tgggcctgag ctggagaagc ctggcgcttc agtgaagata      60
tcctgcaagg cttctggtta ctcattcact ggctacacca tgaactgggt gaagcagagc     120
catgaaaga gccttgagtg gattggactt attactcctt acaatggtgc ttctagctac     180
aaccagaagt tcaggggcaa ggccacatta actgtagaca agtcatccag cacagcctac     240
atggacctcc tcagtctgac atctgaagac tctgcagtct atttctgtgc aaggggggggt     300
tacgacggga ggggttttga ctactggggc caagggacca cggtcaccgt ctcctcaggt     360
gtaggcggtt caggcggcgg tggctctggc ggtggcggat cggacatcga gctcactcag     420
tctccagcaa tcatgtctgc atctccaggg gagaaggtca ccatgacctg cagtgccagc     480
tcaagtgtaa gttacatgca ctggtaccag cagaagtcag gcacctcccc caaaagatgg     540
atttatgaca catccaaact ggcttctgga gtcccaggtc gcttcagtgg cagtgggtct     600
ggaaactctt actctctcac aatcagcagc gtggaggctg aagatgatgc aacttattac     660
tgccagcagt ggagtaagca ccctctcacg ttcggtgctg ggacaaagtt ggaaataaaa     720
taatga                                                                726
```

<210> SEQ ID NO 12
<211> LENGTH: 240
<212> TYPE: PRT
<213> ORGANISM: artificial sequence
<220> FEATURE:
<223> OTHER INFORMATION: SS1

<400> SEQUENCE: 12

```
Gln Val Gln Leu Gln Gln Ser Gly Pro Glu Leu Glu Lys Pro Gly Ala
1               5                  10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Val Gly Gly Ser Gly Gly Gly Gly
        115                 120                 125

Ser Gly Gly Gly Gly Ser Asp Ile Glu Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175
```

```
Pro Lys Arg Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
        195                 200                 205

Ser Ser Val Glu Ala Glu Asp Asp Ala Thr Tyr Tyr Cys Gln Gln Trp
210                 215                 220

Ser Lys His Pro Leu Thr Phe Gly Ala Gly Thr Lys Leu Glu Ile Lys
225                 230                 235                 240
```

<210> SEQ ID NO 13
<211> LENGTH: 109
<212> TYPE: DNA
<213> ORGANISM: artificial sequence
<220> FEATURE:
<223> OTHER INFORMATION: PCR Primer

<400> SEQUENCE: 13

```
ggaagcgttg gcgcatatgg gcattctggg cttcgtgttt accctgggcg gaggaggatc      60
cggtggcgga ggttcaggag gcggtggatc gatccagcgt actccaaag                 109
```

<210> SEQ ID NO 14
<211> LENGTH: 38
<212> TYPE: DNA
<213> ORGANISM: artificial sequence
<220> FEATURE:
<223> OTHER INFORMATION: PCR primer

<400> SEQUENCE: 14

```
gcagtaagga attctcatta ttttatttcc aactttgt                              38
```

<210> SEQ ID NO 15
<211> LENGTH: 56
<212> TYPE: DNA
<213> ORGANISM: artificial sequence
<220> FEATURE:
<223> OTHER INFORMATION: PCR primer

<400> SEQUENCE: 15

```
tatgaacctg gtgccgatgg tcgcgaccgt tggaggtggc ggttctggcg gaggag          56
```

<210> SEQ ID NO 16
<211> LENGTH: 58
<212> TYPE: DNA
<213> ORGANISM: artificial sequence
<220> FEATURE:
<223> OTHER INFORMATION: PCR primer

<400> SEQUENCE: 16

```
gatcctcctc cgccagaacc gccacctcca acggtcgcga ccatcggcac caggttca        58
```

<210> SEQ ID NO 17
<211> LENGTH: 108
<212> TYPE: DNA
<213> ORGANISM: artificial sequence
<220> FEATURE:
<223> OTHER INFORMATION: PCR primer

<400> SEQUENCE: 17

```
ggaagcgttg gcgcatatga tcatggacca ggttccgttc tctgttggcg aggagggtcc      60
ggtggcggag gttcaggagg cggtggatcg atccagcgta ctccaaag                  108
```

<210> SEQ ID NO 18
<211> LENGTH: 38
<212> TYPE: DNA

```
<213> ORGANISM: artificial sequence
<220> FEATURE:
<223> OTHER INFORMATION: PCR primer

<400> SEQUENCE: 18
gcagtaagga attctcatta ttttatttcc aactttgt                              38

<210> SEQ ID NO 19
<211> LENGTH: 15
<212> TYPE: PRT
<213> ORGANISM: artificial sequence
<220> FEATURE:
<223> OTHER INFORMATION: peptide linker

<400> SEQUENCE: 19

Gly Val Gly Gly Ser Gly Gly Gly Ser Gly Gly Gly Gly Ser
1               5                   10                  15

<210> SEQ ID NO 20
<211> LENGTH: 5
<212> TYPE: PRT
<213> ORGANISM: artificial sequence
<220> FEATURE:
<223> OTHER INFORMATION: peptide linker monomer
<220> FEATURE:
<221> NAME/KEY: MISC_FEATURE
<223> OTHER INFORMATION: X = any amino acid
<220> FEATURE:
<221> NAME/KEY: misc_feature
<222> LOCATION: (2)..(2)
<223> OTHER INFORMATION: Xaa can be any naturally occurring amino acid

<400> SEQUENCE: 20

Gly Xaa Gly Gly Ser
1               5

<210> SEQ ID NO 21
<211> LENGTH: 9
<212> TYPE: PRT
<213> ORGANISM: artificial sequence
<220> FEATURE:
<223> OTHER INFORMATION: peptide linker

<400> SEQUENCE: 21

Gly Ile Leu Gly Phe Val Phe Thr Leu
1               5

<210> SEQ ID NO 22
<211> LENGTH: 1980
<212> TYPE: DNA
<213> ORGANISM: artificial sequence
<220> FEATURE:
<223> OTHER INFORMATION: compound B fusion protein

<400> SEQUENCE: 22
atgaacctgg tgccgatggt cgcgaccgtt ggcggaggag gatccggtgg cggaggttca      60
ggaggcggtg gatcgatcca gcgtactcca aagattcagg tttactcacg tcatccagca     120
gagaatggaa agtcaaattt cctgaattgc tatgtgtctg gtttcatcc atccgacatt      180 gaagttgact tactgaagaa tggagagaga attgaaaaag tggagcattc agacttgtct     240 tttttcgaagg actggtcttt ctatctcttg tactacactg aattcacccc cactgaaaaa     300
gatgagtatg cctgccgtgt gaaccatgtg actttgtcac agcccaagat agttaagtgg     360
gatcgcgaca tgggtggcgg tggaagcggc ggtggaggct ctggtggagg tgcagcggc     420 tctcactcca tgaggtattt cttcacatcc gtgtcccggc ccggccgcgg ggagccccgc     480
```

| | |
|---|---|
| ttcatcgcag tgggctacgt ggacgacacg cagttcgtgc ggttcgacag cgacgccgcg | 540 |
| agccagagga tggagccgcg ggcgccgtgg atagagcagg agggtccgga gtattgggac | 600 |
| ggggagacac ggaaagtgaa ggcccactca cagactcacc gagtggacct ggggaccctg | 660 |
| cgcggctact acaaccagag cgaggccggt tctcacaccg tccagaggat gtatggctgc | 720 |
| gacgtggggt cggactggcg cttcctccgc gggtaccacc agtacgcgta cgacggcaag | 780 |
| gattacatcg ccctgaaaga ggacctgcgc tcttggaccg cggcggacat ggcagctcag | 840 |
| accaccaagc acaagtggga ggcggcccat gtagcggagc agttgagagc ctacctggag | 900 |
| ggcacgtgcg tggagtggct ccgcagatac ctggagaacg gaaggagac gctgcagcgc | 960 |
| acggacgccc ccaaaacgca catgactcac cacgctgtct ctgaccatga agccaccctg | 1020 |
| aggtgctggg ccctgagctt ctaccctgcg gagatcacac tgacctggca gcgggatggg | 1080 |
| gaggaccaga cccaggacac ggagctcgtg gagaccaggc ctgcagggga tggaaccttc | 1140 |
| cagaagtggg cggctgtggt ggtgccttct ggacaggagc agagatacac ctgccatgtg | 1200 |
| cagcatgagg gtttgcccaa gcccctcacc ctgagatggg aggcttccgg aggtcaggta | 1260 |
| caactgcagc agtctgggcc tgagctggag aagcctggcg cttcagtgaa gatatcctgc | 1320 |
| aaggcttctg gttactcatt cactggctac accatgaact gggtgaagca gagccatgga | 1380 |
| aagagccttg agtggattgg acttattact ccttacaatg gtgcttctag ctacaaccag | 1440 |
| aagttcaggg gcaaggccac attaactgta gacaagtcat ccagcacagc ctacatggac | 1500 |
| ctcctcagtc tgacatctga agactctgca gtctatttct gtgcaagggg gggttacgac | 1560 |
| gggaggggtt ttgactactg gggccaaggg accacggtca ccgtctcctc aggtgtaggc | 1620 |
| ggttcaggcg gcggtggctc tggcggtggc ggatcggaca tcgagctcac tcagtctcca | 1680 |
| gcaatcatgt ctgcatctcc aggggagaag gtcaccatga cctgcagtgc cagctcaagt | 1740 |
| gtaagttaca tgcactggta ccagcagaag tcaggcacct cccccaaaag atggatttat | 1800 |
| gacacatcca aactggcttc tggagtccca ggtcgcttca gtggcagtgg gtctgggaac | 1860 |
| tcttactctc tcacaatcag cagcgtggag gctgaagatg atgcaactta ttactgccag | 1920 |
| cagtggagta agcaccctct cacgttcggt gctgggacaa gttggaaat aaaataatga | 1980 |

<210> SEQ ID NO 23
<211> LENGTH: 1980
<212> TYPE: DNA
<213> ORGANISM: artificial sequence
<220> FEATURE:
<223> OTHER INFORMATION: M1cov/scHLA-A2/SS1 (scFv) fusion protein

<400> SEQUENCE: 23

| | |
|---|---|
| atgggcattc tgggcttcgt gtttaccctg gcggaggag atccggtgg cggaggttca | 60 |
| ggaggcggtg gatcgatcca gcgtactcca aagattcagg tttactcacg tcatccagca | 120 |
| gagaatggaa agtcaaattt cctgaattgc tatgtgtctg gtttcatcc atccgacatt | 180 |
| gaagttgact tactgaagaa tggagagaga attgaaaaag tggagcattc agacttgtct | 240 |
| ttttcgaagg actggtcttt ctatctcttg tactacactg aattcacccc cactgaaaaa | 300 |
| gatgagtatg cctgccgtgt gaaccatgtg actttgtcac agcccaagat agttaagtgg | 360 |
| gatcgcgaca tgggtggcgg tggaagcggc ggtggaggct ctggtggagg tggcagcggc | 420 |
| tctcactcca tgaggtattt cttcacatcc gtgtcccggc ccggccgcgg ggagccccgc | 480 |
| ttcatcgcag tgggctacgt ggacgacacg cagttcgtgc ggttcgacag cgacgccgcg | 540 |
| agccagagga tggagccgcg ggcgccgtgg atagagcagg agggtccgga gtattgggac | 600 |

-continued

```
ggggagacac ggaaagtgaa ggcccactca cagactcacc gagtggacct ggggaccctg    660
cgcggctact acaaccagag cgaggccggt tctcacaccg tccagaggat gtatggctgc    720
gacgtggggt cggactggcg cttcctccgc gggtaccacc agtacgcgta cgacggcaag    780
gattacatcg ccctgaaaga ggacctgcgc tcttggaccg cggcggacat ggcagctcag    840
accaccaagc acaagtggga ggcggcccat gtagcggagc agttgagagc ctacctggag    900
ggcacgtgcg tggagtggct ccgcagatac ctggagaacg ggaaggagac gctgcagcgc    960
acggacgccc ccaaaacgca catgactcac cacgctgtct ctgaccatga agccaccctg   1020
aggtgctggg ccctgagctt ctaccctgcg gaaatcacac tgacctggca gcgggatggg   1080
gaggaccaga cccaggacac ggagctcgtg gagaccaggc ctgcagggga tggaaccttc   1140
cagaagtggg cggctgtggt ggtgccttct ggacaggagc agagatacac ctgccatgtg   1200
cagcatgagg gtttgcccaa gccccteacc ctgagatggg aggcttccgg aggtcaggta   1260
caactgcagc agtctgggcc tgagctggag aagcctggcg cttcagtgaa gatatcctgc   1320
aaggcttctg gttactcatt cactggctac accatgaact gggtgaagca gagccatgga   1380
aagagccttg agtggattgg acttattact ccttacaatg gtgcttctag ctacaaccag   1440
aagttcaggg gcaaggccac attaactgta gacaagtcat ccagcacagc ctacatggac   1500
ctcctcagtc tgacatctga agactctgca gtctatttct gtgcaagggg gggttacgac   1560
gggagggggtt ttgactactg gggccaaggg accacggtca ccgtctcctc aggtgtaggc   1620
ggttcaggcg gcggtggctc tggcggtggc ggatcggaca tcgagctcac tcagtctcca   1680
gcaatcatgt ctgcatctcc aggggagaag gtcaccatga cctgcagtgc cagctcaagt   1740
gtaagttaca tgcactggta ccagcagaag tcaggcacct cccccaaaag atggatttat   1800
gacacatcca aactggcttc tggagtccca ggtcgcttca gtggcagtgg gtctgggaac   1860
tcttactctc tcacaatcag cagcgtggag gctgaagatg atgcaactta ttactgccag   1920
cagtggagta agcaccctct cacgttcggt gctgggacaa agttggaaat aaaataatga   1980
```